(12) United States Patent
Bachar

(10) Patent No.: US 10,507,122 B2
(45) Date of Patent: Dec. 17, 2019

(54) RETRACTING OR/AND SUPPORTING PERIURETHRAL TISSUE

(71) Applicant: BUTTERFLY MEDICAL LTD., Yokneam Yilit (IL)

(72) Inventor: Yehuda Bachar, Givaat Shmuel (IL)

(73) Assignee: BUTTERFLY MEDICAL LTD., Yokneam Yilit (IL)

( * ) Notice: Subject to any disclaimer, the term of this patent is extended or adjusted under 35 U.S.C. 154(b) by 3 days.

(21) Appl. No.: 15/747,940

(22) PCT Filed: Jul. 29, 2015

(86) PCT No.: PCT/IB2015/055731
§ 371 (c)(1),
(2) Date: Jan. 26, 2018

(87) PCT Pub. No.: WO2017/017499
PCT Pub. Date: Feb. 2, 2017

(65) Prior Publication Data
US 2018/0214285 A1    Aug. 2, 2018

(51) Int. Cl.
*A61F 2/82*    (2013.01)
*A61M 29/00*    (2006.01)
(Continued)

(52) U.S. Cl.
CPC .................. *A61F 2/82* (2013.01); *A61F 2/04* (2013.01); *A61M 29/00* (2013.01); *A61B 2017/00274* (2013.01); *A61F 2002/047* (2013.01)

(58) Field of Classification Search
CPC ........ A61F 2/82; A61F 2/04; A61F 2002/825; A61F 2/844; A61F 2/86; A61F 2/95;
(Continued)

(56) References Cited

U.S. PATENT DOCUMENTS

| 5,269,802 A | 12/1993 | Garber |
| 5,496,365 A | 3/1996 | Sgro |

(Continued)

FOREIGN PATENT DOCUMENTS

| CN | 106102655 | 11/2016 |
| WO | 2010073244 A2 | 7/2010 |

(Continued)

OTHER PUBLICATIONS

May 11, 2016 International Search Report issued in International Application No. PCT/IB2015/055731.

*Primary Examiner* — Paul B Prebilic

(57) ABSTRACT

Urological (prostatic) implant, system, and method for retracting or/and supporting periurethral tissue enclosing a prostatic urethra along lengths of prostate lobes, for example, in BPH patients. Prostatic implant includes independently actuatable distal retractor incorporating craniolateral corners and proximal retractor incorporating caudolateral corners. Retractors may be connected via elongated spine member, and formed as paired curved wing-liked structures having interconnecting members. May further include tissue support members extending between elongated edge members connecting retractors to spine member, and tissue support members extending between elongated edge members and spine member. Tissue support members are sized and configured for supporting portions of prostatic lateral lobes when spine member engages anterior interlobar groove extending between prostatic lateral lobes, and when elongated edge members engage posterolateral interlobar grooves. System and method include implant manipulator detachably connected to implant elongated edge members, for manipulating and forcing implant caudolateral corners into close proximity, for delivery into subject.

36 Claims, 10 Drawing Sheets

(51) Int. Cl.
*A61F 2/04* (2013.01)
*A61B 17/00* (2006.01)

(58) Field of Classification Search
CPC ...... A61F 2002/9505; A61F 2002/9522; A61F 2/962; A61F 2230/0054; A61F 2250/0006; A61F 2250/001; A61F 2002/047; A61M 29/00
See application file for complete search history.

(56) References Cited

U.S. PATENT DOCUMENTS

| | | | |
|---|---|---|---|
| 6,994,093 B2* | 2/2006 | Murphy | A61B 17/0218 |
| | | | 128/898 |
| 8,591,569 B2 | 11/2013 | Shin et al. | |
| 8,603,187 B2* | 12/2013 | Kilemnick | A61B 18/02 |
| | | | 606/157 |
| 10,105,132 B2* | 10/2018 | Lamson | A61F 2/82 |
| 2002/0010487 A1* | 1/2002 | Evans | A61B 17/221 |
| | | | 606/180 |
| 2002/0029075 A1* | 3/2002 | Leonhardt | A61F 2/07 |
| | | | 623/1.11 |
| 2003/0040803 A1 | 2/2003 | Rioux et al. | |
| 2003/0060870 A1* | 3/2003 | Reever | A61F 2/88 |
| | | | 623/1.12 |
| 2003/0069647 A1 | 4/2003 | Joseph, III et al. | |
| 2004/0144395 A1* | 7/2004 | Evans | A61B 17/06066 |
| | | | 128/885 |
| 2004/0167635 A1 | 8/2004 | Yachia et al. | |
| 2008/0065209 A1* | 3/2008 | Pflueger | A61F 2/203 |
| | | | 623/9 |
| 2009/0156977 A1* | 6/2009 | Daignault | A61F 2/04 |
| | | | 604/8 |
| 2010/0137893 A1 | 6/2010 | Kilemnick et al. | |
| 2011/0098825 A1 | 4/2011 | Shin et al. | |
| 2014/0012192 A1* | 1/2014 | Bar-On | A61F 2/04 |
| | | | 604/93.01 |

FOREIGN PATENT DOCUMENTS

| | | | | |
|---|---|---|---|---|
| WO | | 2015101975 A1 | 7/2015 | |
| WO | | 2015111063 A1 | 7/2015 | |
| WO | WO | 2019111247 A1 * | 6/2019 | ............ A61F 2/04 |

* cited by examiner

RETRACTING OR/AND SUPPORTING PERIURETHRAL TISSUE

FIELD OF THE INVENTION

The present invention, in some embodiments thereof, relates to the field of urological medical devices and applications thereof, and more particularly, but not exclusively, to a urological (prostatic) implant, system, and method for retracting or/and supporting periurethral tissue enclosing a prostatic urethra along a length of prostate lobes.

BACKGROUND OF THE INVENTION

Benign prostate hyperplasia (BPH), also known as benign prostatic hypertrophy, is a urological disease in which the prostate enlarges and constricts the urethra. BPH affects a majority of the male population over 50 years of age, and is thus of great medical and commercial importance.

Surgical treatment of hypertrophy of the prostate has been a routine procedure for many years. One method of such surgical treatment is open prostatectomy wherein the gland is totally or partially removed. Another method of surgical treatment is transurethral resection of the prostate (TURP). Surgical treatment is an invasive procedure that may be debilitating, painful and traumatic to the patient. Such surgical treatment may result in various complications including impotence, incontinence, bleeding, infection, and other undesirable problems.

Another procedure to treat prostatic hypertrophy is to place a catheter at the external opening of the urethra and into the obstructed portions of the urethra, allowing urine to pass from the bladder by way of the catheter lumen. These urinary catheters typically employ a positioning or retention balloon at the distal tip which inflates at the bladder neck and prevents the expulsion of the catheter from the body.

Ablation techniques based on using heat, such as produced by microwave or laser energy, may be provided in combination with such catheters for treating the enlarged portion of the prostate. However, such a procedure may result in pain and discomfort to the patient.

In spite of extensive teachings and practices in the field of urology, there is an on-going need for developing and practicing improved and new urological medical devices and applications thereof, for treating benign prostate hyperplasia (BPH).

SUMMARY OF THE INVENTION

The present invention, in some embodiments thereof, relates to a urological (prostatic) implant, system, and method for retracting or/and supporting periurethral tissue enclosing a prostatic urethra along a length of prostate lobes.

According to an aspect of some embodiments of the present invention, there is provided an implant for retracting or/and supporting periurethral tissue enclosing a prostatic urethra along a length of prostate lobes, the implant comprising: a distal retractor incorporating a first and a second craniolateral corners; and a proximal retractor incorporating a first and a second caudolateral corners; wherein said distal retractor and proximal retractor are independently actuatable.

According to some embodiments of the invention, the distal retractor is connected to, or integrally formed as a single structure with, the proximal retractor, via an elongated spine member extending along a spinal longitudinal axis or/and a plurality of elongated edge members.

According to some embodiments of the invention, the distal retractor or/and the proximal retractor are in a form of a pair of curved wing-like structures connected to the spine member via interconnecting members, and symmetrically opposing each other relative to the spinal longitudinal axis.

According to some embodiments of the invention, each the interconnecting members includes at least one elastic portion adjoining the spine member, the elastic portion being non-stressed when a first of the curved wing-like structures in the pair is pivotally positioned centrally away from a second of the curved wing-like structures in the pair about the spinal longitudinal axis, so as to form a predetermined maximal elongated edge member spanning angle. Optionally, the at least one elastic portion exhibits an increase in stress when subjected to a moment of force that pivotally shifts the first curved wing-like structure towards the second curved wing-like structure about the spinal longitudinal axis.

According to some embodiments of the invention, the implant further comprises at least one tissue support member extending between a first elongated edge member and the spinal longitudinal axis, and at least one other tissue support member extending between a second elongated edge member and the spinal longitudinal axis, wherein each tissue support member is sized and configured for supporting a portion of a prostatic lateral lobe when the spine member engages an anterior interlobar groove that extends between prostatic lateral lobes in the prostate, and when the first and second elongated edge members engage corresponding posterolateral interlobar grooves. Optionally, the spine member has a length being equal to or less than length of the anterior interlobar groove or/and substantially less than length of each of the first and second elongated edge members. Optionally, the first elongated edge member is sized for positioning in a left posterolateral interlobar groove that extends between a left prostatic lateral lobe and a prostatic medial lobe, and the second elongated edge member is sized for positioning in a right posterolateral interlobar groove that extends between a right prostatic lateral lobe and the prostatic medial lobe.

According to an aspect of some embodiments of the present invention, there is provided an implant for retracting or/and supporting periurethral tissue enclosing a prostatic urethra along a length of prostate lobes, the implant comprising: an elongated spine member having a spinal longitudinal axis. a first elongated edge member and a second elongated edge member symmetrically opposing each other relative to the spinal longitudinal axis, each elongated edge member is interconnected to the spine member via at least one interconnecting member.

According to some embodiments of the invention, at least one tissue support member extending to between the first elongated edge member and the spinal longitudinal axis, and at least one other tissue support member extending between the second elongated edge member and the spinal longitudinal axis, wherein each tissue support member is sized and configured for supporting a portion of a prostatic lateral lobe when the spine member engages an anterior interlobar groove that extends between prostatic lateral lobes in the prostate, and when the first and second elongated edge members engage corresponding posterolateral interlobar grooves.

According to some embodiments of the invention, the spine member has a length being equal to or less than length of the anterior interlobar groove or/and substantially less than length of each of the first and second elongated edge members. Optionally, the first elongated edge member is sized for positioning in a left posterolateral interlobar groove that extends between a left prostatic lateral lobe and a prostatic medial lobe, and the second elongated edge member is sized for positioning in a right posterolateral interlobar groove that extends between a right prostatic lateral lobe and the prostatic medial lobe.

According to some embodiments of the invention, each of the interconnecting members includes at least one elastic portion adjoining the spine member, the elastic portion being non-stressed when the first and second elongated edge members are pivotally positioned centrally away from each other about the spinal longitudinal axis, so as to form a predetermined maximal spanning angle between opposing the interconnecting members. Optionally, the predetermined maximal spanning angle is within a range of between about 60° and about 140°. Optionally, the at least one elastic portion exhibits an increase in stress when subjected to a moment of force that pivotally shifts the first and second elongated edge members towards each other about the spinal longitudinal axis. Optionally, the first and second edge members are configured to approach each other so as to form a spanning angle between opposing the interconnecting members being equal to or greater than about 60°, when each first and second elongated edge member or/and each tissue support member exerts a total lateral pressing force upon a corresponding prostatic lateral lobe, the total lateral pressing force being a range of between about 100 grams and about 1,000 grams.

According to some embodiments of the invention, wherein the at least one tissue support member is configured as a curvilinear portion of the first or/and second elongated edge member protruding towards the spinal longitudinal axis.

According to some embodiments of the invention, wherein the at least one tissue support member is configured as a curvilinear portion of the first or/and second elongated edge member that protrudes laterally outwardly from an area encompassed by the first or/and second elongated edge member and the spine member.

According to some embodiments of the invention, the at least one tissue support member is configured as a rib or rib-type member extending from one of the interconnecting members. Optionally, the rib or rib-type member is curved or bent laterally outwardly from a perimeter of area encompassed by a corresponding the elongated edge member and the spine member.

According to some embodiments of the invention, the at least one tissue support member comprises a tissue contacting surface sized or/and shaped according to dimensions of the prostatic lateral lobe portion.

According to some embodiments of the invention, the left and right posterolateral interlobar grooves, by continuously exerting a radially directed pushing force thereupon, within a range of between about 100 grams and about 1,000 grams, so as to prevent or minimize axial or/and rotational movement of the anchored anterior interlobar groove, and, the left and right posterolateral interlobar grooves.

According to some embodiments of the invention, the implant is configured to anchor the anterior interlobar groove, and, the left and right posterolateral interlobar grooves, by continuously exerting a radially directed pushing force thereupon, so as to increase distance separating superior portions of the interlobar grooves and increase distance separating left and right inferior portions of the interlobar grooves, or/and to maintain a distance of at least 2 mm between the prostatic lateral lobes, by exerting lateral forces thereupon within a range of between about 100 grams and about 1,000 grams.

According to some embodiments of the invention, at least one of the first and second elongated edge members comprises a cranial-nose portion shaped and configured for resting against a ledge, imposed by a urinary bladder neck segment adjacent the prostatic urethra, so as to prevent cranial dislodgment of the implant into urinary bladder, when the spine member engages an anterior interlobar groove that extends between the prostatic lateral lobes, and when the first and second elongated edge members engage corresponding posterolateral interlobar grooves. Optionally, the cranial-nose portion is "L" shaped.

According to some embodiments of the invention, at least one of the first and second elongated edge members comprises a caudal-nose portion shaped and configured for resting against a narrowing, imposed by external urethral sphincter adjacent to verumontanum of the prostatic urethra, so as to prevent caudal migration of the implant through external sphincter and into bulbar urethra, when the spine member engages an anterior interlobar groove that extends between the prostatic lateral lobes, and when the first and second elongated edge members engage corresponding posterolateral interlobar grooves. Optionally, the caudal-nose portion is "L" shaped.

According to an aspect of some embodiments of the present invention, there is provided a system for retracting or/and supporting periurethral tissue enclosing a prostatic urethra along a length of prostate lobes, the system comprising an implant comprising a plurality of elongated edge members interconnected in a form of a collapsible-expandable frame expandable to retract or/and support periurethral tissue by exerting pushing forces upon interlobar grooves located along the prostatic urethra, wherein a first one of the elongated edge members includes a first craniolateral corner and a first caudolateral corner, and a second one of the elongated edge members includes a second craniolateral corner opposing the first craniolateral corner and a second caudolateral corner opposing the first caudolateral corner.

According to some embodiments of the invention, the implant manipulator detachably connected to the implant first and second elongated edge members, and configured to manipulate and force the first and second caudolateral corners into close proximity with each other. configured for progressively or sequentially changing shape or form of the implant according to different progressive or sequential implant deployment configurations including at least one of: a fully collapsed delivery configuration, whereby the first and second craniolateral corners are in close proximity with each other, and, the first and second caudolateral corners are in close proximity with each other; a partially collapsed positioning configuration, whereby the first and second craniolateral corners are distanced apart from each other, and, the first and second caudolateral corners are in close proximity with each other; and an expanded deployed configuration, whereby the first and second craniolateral corners are distanced apart from each other, and, the first and second caudolateral corners are distanced apart from each other.

According to some embodiments of the invention, the implant manipulator, when connected to the implant, is configured for applying thereto at least one of rotational forces, pulling forces, and pushing forces.

According to some embodiments of the invention, the implant manipulator comprises a tubular member and a tether releasably intertwined through both of the implant first and second caudolateral corners, the implant manipulator is configured for continuously or/and selectively pulling the implant via an operator using the tether against a distal end of the tubular member.

According to some embodiments of the invention, the system further comprises an over sheath sized for covering a length of a cystoscope having a cystoscope lumen dimensioned to restrain the implant in the fully collapsed delivery configuration via at least encircling the implant first and second craniolateral corners.

According to some embodiments of the invention, the implant manipulator is configured for facilitating and effecting the progressively or sequentially changing shape or form of the implant according to the different progressive or sequential implant deployment configurations. Optionally, the implant manipulator is configured for manipulating and shifting the implant within the over-sheath between the fully collapsed delivery configuration and the partially collapsed positioning configuration, by pushing or pulling the implant relative to the over-sheath lumen until the implant first and second craniolateral corners are released from the implant manipulator over sheath.

According to some embodiments of the invention, the implant manipulator is configured for manipulating and shifting the implant between the partially collapsed delivery configuration and the expanded deployed configuration by detaching from the implant after release of the tether from the implant first and second caudolateral corners.

According to some embodiments of the invention, the partially collapsed positioning configuration includes the implant having a frustum or cone-like shape whose distal-most diameter thereof is greater than smallest cross-sectional dimension in a urinary bladder neck joining the prostatic urethra, and whose proximal-most diameter thereof is smaller than the smallest cross-sectional dimension in the urinary bladder neck.

According to some embodiments of the invention, the implant comprises: an elongated spine member having a spinal longitudinal axis; and a first elongated edge member and a second elongated edge member symmetrically opposing each other relative to the spinal longitudinal axis, and interconnected to the spine member via at least one interconnecting member.

Optionally, the spine member has a length being equal to or less than length of an anterior interlobar groove that extends between prostatic lateral lobes, or/and substantially less than length of each of the first and second elongated edge members. Optionally, the first elongated edge member is sized for positioning in a left posterolateral interlobar groove that extends between a left prostatic lateral lobe and a prostatic medial lobe, and the second elongated edge member is sized for positioning in a right posterolateral interlobar groove that extends between a right prostatic lateral lobe and the prostatic medial lobe.

According to some embodiments of the invention, at least one of the implant first and second craniolateral corners are shaped and configured for resting against a ledge imposed by urinary bladder neck so as to prevent cranial dislodgement of the implant into urinary bladder, when the spine member engages an anterior interlobar groove that extends between prostatic lateral lobes, and when the first and second elongated edge members engage corresponding posterolateral interlobar grooves.

According to some embodiments of the invention, at least one of the implant first and second caudolateral corners are shaped and configured for resting against a narrowing imposed by external urethral sphincter adjacent verumontanum of the prostatic urethra, so as to prevent caudal shift of the implant, when the spine member engages an anterior interlobar groove that extends between prostatic lateral lobes, and when the first and second elongated edge members engage corresponding posterolateral interlobar grooves. Optionally, each of the implant first and second caudolateral corners has a shape or form of a proximally directed apex, the apex being formed by intersection of converging curved slopes of respective ones of the implant first and second caudolateral corners.

According to an aspect of some embodiments of the present invention, there is provided a method for retracting or/and supporting periurethral tissue enclosing a prostatic urethra along a length of prostate lobes, the method comprising providing an implant along a chosen length of the prostate lobes. Optionally, the method also includes exerting continuous radially directed pushing forces upon an anterior interlobar groove between the prostate lobes, and upon at least one of left and right posterolateral interlobar grooves between the prostate lobes, thereby anchoring the implant in-place. Optionally, the method also includes exerting lateral pressing forces upon one or more prostatic lateral lobes, thereby retracting or/and supporting the periurethral tissue.

According to an aspect of some embodiments of the present invention, there is provided a method for retracting or/and supporting periurethral tissue enclosing a prostatic urethra along a length of prostate lobes, the method comprising providing an implant in a fully collapsed delivery configuration, the implant comprises an independently actuatable distal retractor incorporating first and second craniolateral corners, and an independently actuatable proximal retractor incorporating first and second caudolateral corners, wherein the first and second craniolateral corners are in close proximity to each other, and, the first and second caudolateral corners are in close proximity to each other.

Optionally, the method also includes passing the implant in the fully collapsed delivery configuration, in a cranial direction in a subject's urethra, into the subject's urinary bladder. Optionally, the method also includes expanding the distal retractor within inner boundaries of the urinary bladder. Optionally, the method also includes positioning under vision the implant in the prostatic urethra along the length of the prostate lobes. Optionally, the method also includes expanding the proximal retractor so as to effect changing configuration of the implant from the fully collapsed delivery configuration into an expanded deployed configuration, wherein the first and second craniolateral corners are distanced apart from each other, and, the first and second caudolateral corners are distanced apart from each other.

According to some embodiments of the invention, the providing includes collapsing the implant from a non-stressed fully opened configuration to the fully collapsed delivery configuration.

According to some embodiments of the invention, the collapsing includes at least one of: urging the first and second caudolateral corners into the close approximation therebetween, using an implant manipulator, so as to effect the implant into the partially collapsed positioning configuration; and drawing a compression sleeve over entire length of the implant, the compression sleeve incorporates a lumen sized for effecting the implant from the partially collapsed positioning configuration into the fully collapsed delivery configuration.

According to some embodiments of the invention, the urging includes pulling a tether, releasably intertwined through both the first and second caudolateral corners, against a distal end of a tubular member forming the implant manipulator.

According to some embodiments of the invention, the passing includes at least one of loading the implant manipulator with the implant connected thereto into a lumen of a urologic cystoscope; and pushing the implant distally through the urethra with the urologic cystoscope.

Optionally, the method also includes sleeving an over-sheath over a longitudinal body of the urologic cystoscope; and extending the over-sheath throughout length of the urethra with a distal end thereof provided adjacent or inside the urinary bladder. Optionally, the positioning or the expanding the proximal retractor includes or is preceded by removing the urologic cystoscope.

According to some embodiments of the invention, expanding the distal retractor effects the implant into a partially collapsed positioning configuration, whereby the first and second craniolateral corners are distanced one with each other, and, the first and second caudolateral corners are kept in close approximation therebetween.

Optionally, expanding the distal retractor includes releasing the distal retractor from a restricting boundary until the distal retractor protrudes in a cranial direction from a distal end of the over-sheath inner lumen.

According to some embodiments of the invention, the distal implant comprises an elongated spine member extending along a spinal longitudinal axis, and a first and a second elongated edge members connected to the spine member via interconnecting members, and symmetrically opposing each other relative to the spinal longitudinal axis. Optionally, the spine member is sized for positioning in an anterior interlobar groove that extends between lateral prostate lobes in the prostatic urethra. Optionally, the first elongated edge member is sized for positioning in a left posterolateral interlobar groove that extends between a left lateral prostate lobe and a middle prostate lobe, and the second elongated edge member is sized for positioning in a right posterolateral interlobar groove that extends between a right lateral prostate lobe and a middle prostate lobe.

According to some embodiments of the invention, positioning includes: rotating the implant, by applying torque forces, relative to the spinal longitudinal axis so as to align the spine member with the anterior interlobar groove, or/and to align the first elongated edge member with the left posterolateral interlobar groove, or/and to align the second elongated edge member with the right posterolateral interlobar groove; and visually verifying the alignment using cystoscopy.

According to some embodiments of the invention, positioning includes pulling the implant in a caudal direction to a position within the prostatic urethra or/and placing the first and second craniolateral corners against a narrowing imposed by internal urethral sphincter adjacent to urine-bladder neck. Optionally, positioning includes inserting the spine member in the anterior interlobar groove, or/and inserting the first elongated edge member in the left posterolateral interlobar groove, or/and inserting the second elongated edge member in the right posterolateral interlobar groove.

According to some embodiments of the invention, positioning results in the implant, being in the partially collapsed positioning configuration, expanding a distal region of the prostatic urethra, using the distal retractor, into a greater lumen size than an adjacent proximal region of the prosthetic urethra.

According to some embodiments of the invention, positioning further results in the distal retractor partially collapsing into conforming with anatomy of the distal region of the prostatic urethra.

According to some embodiments of the invention, the implant comprises at least one tissue support member sized and configured for supporting a portion of a lateral prostatic lobe following the positioning. Optionally, the method further includes:

leaving the implant to continuously exert radially directed pushing forces upon the anterior interlobar groove and at least one of the left and right posterolateral interlobar grooves, so as to prevent or minimize axial or/and rotational movement thereof, or/and to increase distance separating the superior interlobar grooves and to increase distance separating the left and right inferior-lateral interlobar grooves.

According to some embodiments of the invention, leaving the implant includes exerting lateral pressing forces upon each lateral prostate lobe, thereby retracting or/and supporting the periurethral tissue.

Optionally, the method comprises repeating at least one of expanding the distal retractor, positioning and expanding the proximal retractor until reaching a chosen result. Optionally, repeating includes: re-collapsing the implant back into the fully collapsed delivery configuration; and passing the implant back into a urinary bladder.

According to some embodiments of the invention, the chosen result is verified under vision. Optionally, the chosen result includes anchoring different portions of the implant in at least two of anterior interlobar groove, left posterolateral interlobar groove, and right posterolateral interlobar groove of the prostatic urethra within the boundaries of the prostate lobes. Optionally, the chosen result includes lifting both lateral prostate lobes so as to enlarge minimal lumen size of the prostatic urethra to at least 1 mm along a continuous length thereof.

According to some embodiments of the invention, lifting includes shifting each the lateral prostate lobe, pivotally, relatively to the anterior interlobar groove.

All technical or/and scientific words, terms, or/and phrases, used herein have the same or similar meaning as commonly understood by one of ordinary skill in the art to which the invention pertains, unless otherwise specifically defined or stated herein. Methods, materials, and examples described herein are illustrative only and are not intended to be necessarily limiting. Although methods or/and materials equivalent or similar to those described herein can be used in practicing or/and testing embodiments of the invention, exemplary methods or/and materials are described below. In case of conflict, the patent specification, including definitions, will control.

Implementation of some embodiments of the invention can involve performing or completing selected tasks manually, automatically, or a combination thereof. Moreover, according to actual instrumentation and equipment of some embodiments of the invention, several selected tasks could be implemented by hardware, by software, by firmware, or a combination thereof, using a computerized operating system.

BRIEF DESCRIPTION OF THE SEVERAL VIEWS OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings.

DESCRIPTION OF SPECIFIC EMBODIMENTS OF THE INVENTION

The present invention, in some embodiments thereof, relates to the field of urological medical devices and applications thereof, and more particularly, but not exclusively, to a urological (prostatic) implant, system, and method for retracting or/and supporting periurethral tissue enclosing a prostatic urethra along a length of prostate lobes.

As briefly explained hereinabove in the Background section, benign prostate hyperplasia (hypertrophy) (BPH) is commonly treated by surgical techniques, catheter based techniques, or/and ablation techniques, among other known techniques. Treating subjects having BPH by such techniques may involve, or cause, any number of various complications and problems. Such complications and problems may be directly associated with performing a given BPH treatment technique itself, for example, as directly relating to equipment (medical devices) or/and procedures (methods) used in a surgical technique, a catheter based technique, or an ablation technique. Alternatively, or additionally, situations may arise where such complications and problems are not be directly associated with performing a given BPH treatment technique itself, however, they may be an indirect result or unintended consequence (e.g., side effect) during or/and after performing a given BPH treatment technique.

Some embodiments of the presently disclosed invention are suitable for treating subjects having conditions of benign prostate hyperplasia (hypertrophy) (BPH), where such treatment is expected to be absent of various possible complications and problems of, or associated with, known BPH treatment techniques. Accordingly, implementation and practice of some embodiments of the present invention may provide at least some solutions to at least some problems associated with known teachings in the field of urological medical devices and applications thereof that are currently used for treating subjects having BPH.

For purposes of better understanding embodiments of the present invention, in the following illustrative description thereof, reference is made to the figures. Throughout the following description and accompanying drawings, same reference notation and terminology (i.e., numbers, letters, symbols, terms, and phrases) are consistently used and refer to same components, elements, or features. It is to be understood that the invention is not necessarily limited in its application to particular details of construction or/and arrangement of device, apparatus, or/and system components, or to any particular sequential ordering of method steps or procedures, set forth in the following illustrative description. The invention is capable of other embodiments or of being practiced or carried out in various ways.

Figure 1A:
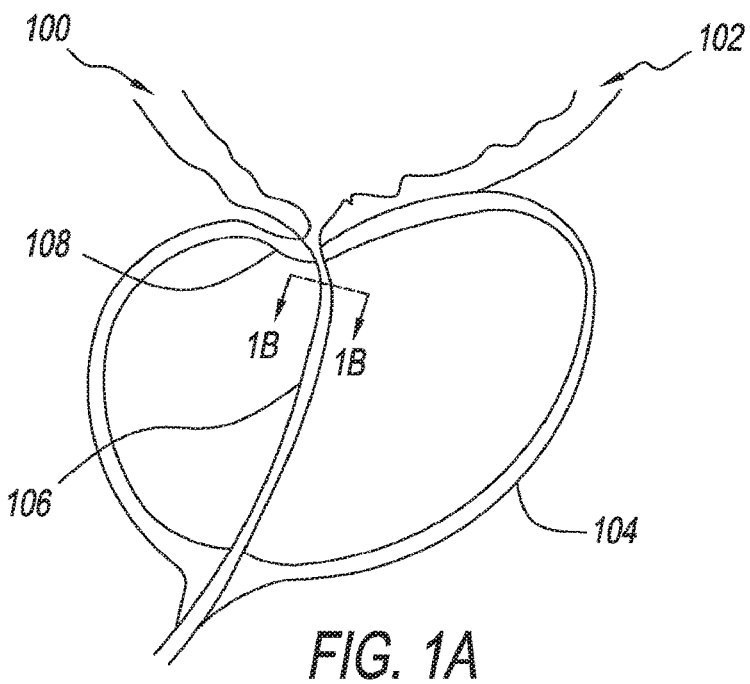
FIG. 1A schematically illustrates a cross sectional side view of a typical human anatomical region encompassing the lower part of the bladder, the prostate, and the prostatic urethra, absent of benign prostate hyperplasia (BPH)

Referring now to the drawings, FIG. 1A schematically illustrates a cross sectional side view of a typical human anatomical region 100 encompassing the lower part of the urinary bladder 102, the prostate 104, and the prostatic urethra 106, where the anatomical region is absent of benign prostate hyperplasia (BPH). The prostatic urethra 106 is surrounded by and extends through the prostate 104 towards the bladder neck 108 of the urinary bladder 102.

Figure 1B:
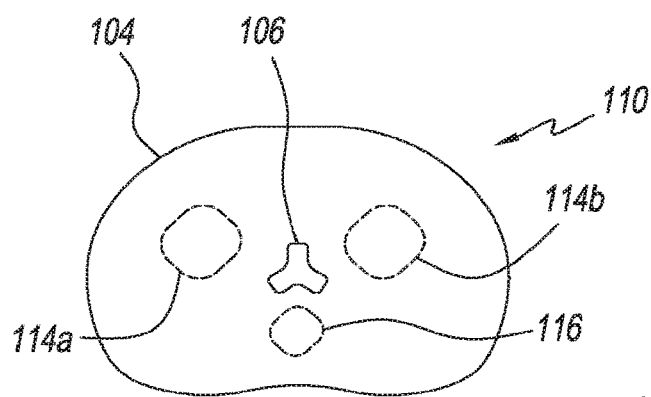
FIG. 1B schematically illustrates a cross sectional top view of a portion of the anatomical region shown in FIG. 1A (dashed line double arrow 1B-1B therein), highlighting exemplary relative positions, configurations, and sizes of a prostatic urethra in a normal open condition and selected prostatic lobes [dashed line circles]

In the context of schematically illustrating and visualizing benign prostate hyperplasia (BPH), of particular interest are characteristics and parameters of, or relating to, position, configuration, and size (diameter) of the prostatic urethra 106 relative to those of the various prostatic lobes of the prostate 104 surrounding the prostatic urethra 106. FIG. 1B schematically illustrates a cross sectional top view of a portion 110 of the anatomical region 100 shown in FIG. 1A (indicated by the dashed line double arrow B-1B therein), highlighting exemplary relative positions, configurations, and sizes of a prostatic urethra 106 in a normal open condition and selected prostatic lobes [dashed line circles], namely, left and right prostatic lateral lobes 114a and 114b, respectively, and prostatic medial lobe 116, during 'normal' conditions absent of BPH.

Figure 1C:
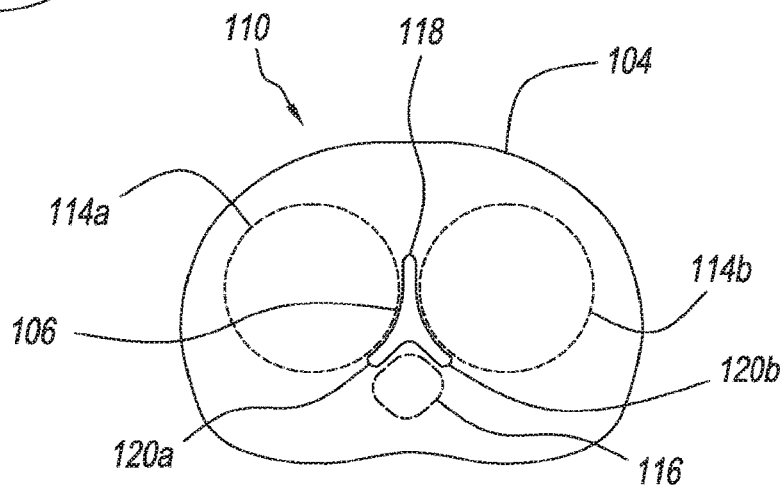
FIG. 1C schematically illustrates a cross sectional top view of the same portion of the anatomical region shown in FIG. 1A, exhibiting benign prostate hyperplasia (BPH), highlighting exemplary relative positions, configurations, and sizes of the prostatic urethra in an abnormal compressed condition and selected prostatic lobes [dashed line circles]

FIG. 1C schematically illustrates a cross sectional top view of the same portion 110 of the anatomical region 100 shown in FIG. 1A, exhibiting benign prostate hyperplasia (BPH), highlighting exemplary relative positions, configurations, and sizes of the prostatic urethra 106 in an abnormal compressed condition and selected prostatic lobes [dashed line circles], namely, left and right prostatic lateral lobes 114a and 114b, respectively, and prostatic medial lobe 116, during 'abnormal' conditions due to BPH. For additional illustrative purposes, FIG. 1C also shows the anterior interlobar groove 118, and, the left and right posterolateral interlobar grooves 120a and 120b, respectively, so formed as a result of 'abnormal' enlargement of prostatic lobes 114a, 114b, and 116, along with 'abnormal' compression of prostatic urethra 106.

In the context of the relevant medical fields relating to, and associated with, the present invention, for the purpose of further enhancing understanding of the illustrative description of the numerous exemplary embodiments of the invention, herein following are meanings of structural and anatomical reference directions used in the hereinbelow illustrative description. The following meanings are presented in a non-limiting manner, whereby, other similar meanings may also be applicable to exemplary embodiments of the herein disclosed invention.

The term 'distal' (direction), as used herein, refers to the direction away from a medical practitioner performing a method or using a device, and closer to a subject's body or towards the midline of the subject's body. The term 'proximal' (direction), as used herein, refers to the direction towards the medical practitioner performing a method or using a device, and farther from a subject's body or away from the midline of the subject's body.

The term 'cranial' (direction), as used herein, refers to the direction generally towards a subject's head or brain, or, for example, in a direction towards a urinary bladder and away from a prostate of same subject. The term 'caudal' (direction), as used herein, refers to the direction opposite that of a subject's head or brain, or/and situated in or directed toward the part of the subject's body from which the tail arises.

The term 'anterior' (direction), as used herein, refers to the direction towards the front plane of a subject's body. The term posterior' (direction), as used herein, refers to the direction towards the rear plane of a subject's body.

The term 'lateral' (direction), as used herein, refers to the direction away from the median and sagittal plane of a subject's body. The term 'medial' (direction), as used herein, refers to the direction towards the median and sagittal plane of a subject's body.

Figure 2A:
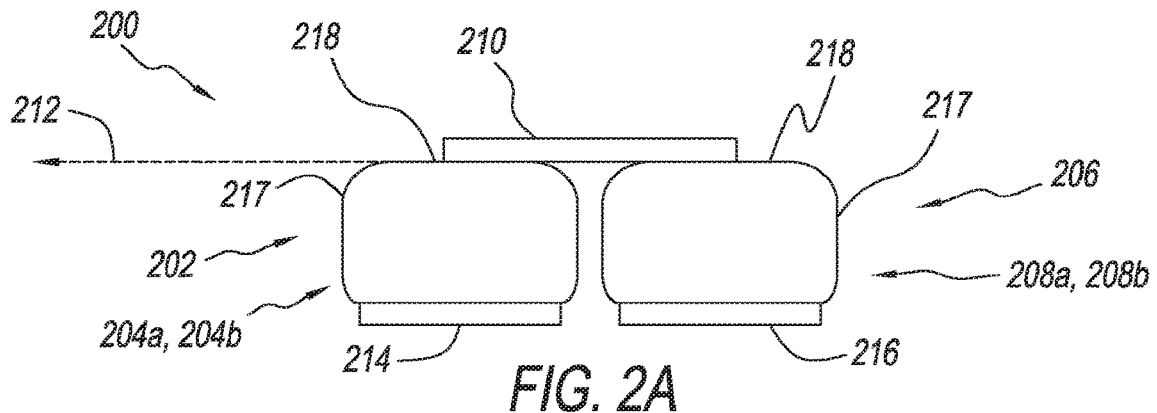
FIG. 2A schematically illustrates a side view of an exemplary embodiment of an implant for retracting or/and supporting periurethral tissue enclosing a prostatic urethra along a length of prostate lobes, highlighting some prostatic implant components, in accordance with some embodiments of the invention.

An aspect of some embodiments of the present invention is an implant (herein, also referred to as a prostatic implant) for retracting or/and supporting periurethral tissue enclosing a prostatic urethra along a length of prostate lobes. FIG. 2A schematically illustrates a side view of an exemplary embodiment of an implant (indicated as, and referred to by, reference number 200) for retracting or/and supporting periurethral tissue enclosing a prostatic urethra along a length of prostate lobes, highlighting some prostatic implant components. Exemplary prostatic implant 200, in a non-limiting manner, includes: a distal retractor 202 incorporating a first craniolateral corner 204a and a second craniolateral corner 204b, and a proximal retractor 206 incorporating a first caudolateral corner 208a and a second caudolateral corner 208b.

In exemplary embodiments, the prostatic implant 200 additionally includes an elongated spine member 210. In such exemplary embodiments, the distal retractor 202 is connected to, or integrally formed as a single structure with, the proximal retractor 206, via the elongated spine member 210 extending along a spinal longitudinal axis 212 or/and a plurality of elongated edge members 214 and 216.

Figure 2B:
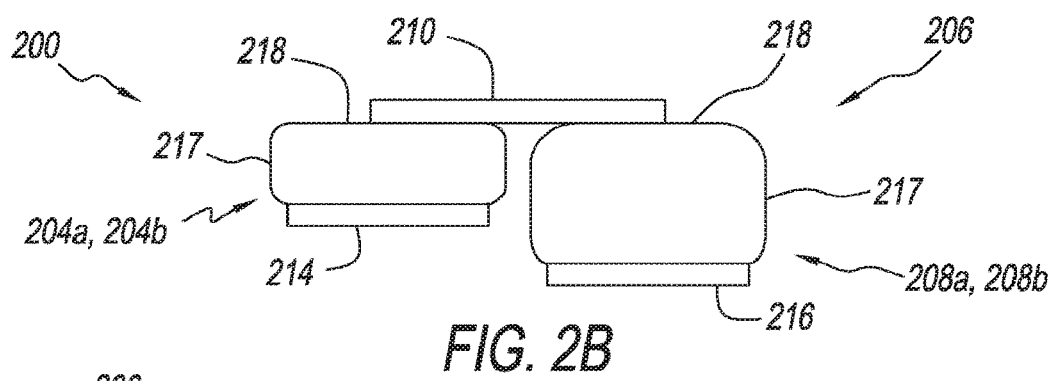
FIG. 2B schematically illustrates the exemplary implant shown in FIG. 2A, highlighting the implant distal retractor exhibiting a non-stressed configuration, and the implant proximal retractor exhibiting a stressed configuration, in accordance with some embodiments of the invention.
Figure 2C:
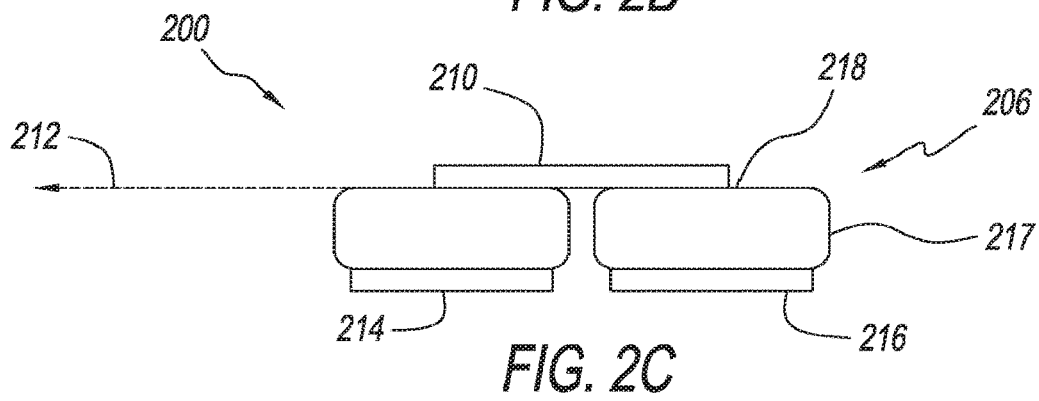
FIG. 2C schematically illustrates the exemplary implant shown in FIG. 2A, highlighting the implant distal and proximal retractors exhibiting a non-stressed configuration, in accordance with some embodiments of the invention.

In exemplary embodiments, the distal retractor 202 and the proximal retractor 206 are independently actuatable. Specifically, actuation (i.e., movement or/and change in configuration, shape or form, or/and position) of the distal retractor 202 is independent of actuation (movement or/and change in configuration, shape or form, or/and position) of the proximal retractor 206, and vice versa. Such independent actuation of the distal retractor 202 and the proximal retractor 206 is exemplified in FIGS. 2B and 2C. FIG. 2B schematically illustrates the exemplary prostatic implant 200 shown in FIG. 2A, highlighting the implant distal retractor 202 exhibiting a non-stressed configuration, and the implant proximal retractor 206 exhibiting a stressed configuration. FIG. 2C schematically illustrates the exemplary prostatic implant 200, highlighting both the implant distal retractor 202 and the proximal retractor 206 exhibiting a non-stressed configuration.

Accordingly, exemplary prostatic implant 200 is capable of undergoing a structural change in a manner whereby, for example, the distal retractor 202 is not actuated and remains in a non-stressed configuration (as shown in both FIGS. 2B and 2C), whereas the proximal retractor 206 is actuated and changes or shifts from a stressed configuration (FIG. 2B) to a non-stressed configuration (FIG. 2C). Such actuation, in the form of configurational change or shift, of the proximal retractor 206 is independent of non-actuation of the distal retractor 202.

Figure 2D:
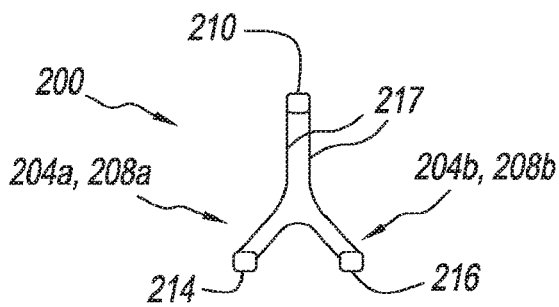
FIG. 2D schematically illustrates a front view of the prostatic implant shown in FIG. 2A exhibiting a stressed configuration, in accordance with some embodiments of the invention.
Figure 2E:
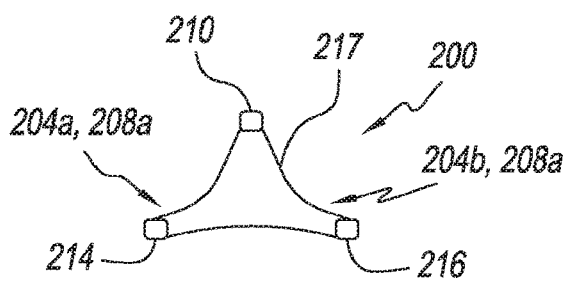
FIG. 2E schematically illustrates a front view of the prostatic implant shown in FIG. 2C exhibiting a non-stressed configuration, in accordance with some embodiments of the invention.

An additional example showing preceding illustratively described structural change of the exemplary prostatic implant 200 is provided in FIGS. 2D-2E. FIG. 2D schematically illustrates a front view of the prostatic implant 200 shown in FIG. 2A exhibiting a stressed configuration, while FIG. 2E schematically illustrates a front view of the prostatic implant 200 shown in FIG. 2C exhibiting a non-stressed configuration. Such structural change of the exemplary prostatic implant 200 (in changing from a stressed configuration of FIG. 2D to a non-stressed configuration of FIG. 2E) is accompanied by radially directed forces outwardly originating from the distal and proximal retractors 202 and 206, respectively, in a manner such that the prostatic implant 200 laterally expands and changes from a stressed configuration (FIG. 2D) to a non-stressed configuration (FIG. 2E).

Exemplary implementation and use of a prostatic implant, for example, prostatic implant 200, for retracting or/and supporting periurethral tissue enclosing a prostatic urethra along a length of prostate lobes, according to some embodiments of the invention, are illustratively described with reference to FIGS. 3A and 3B.

Figure 3A:
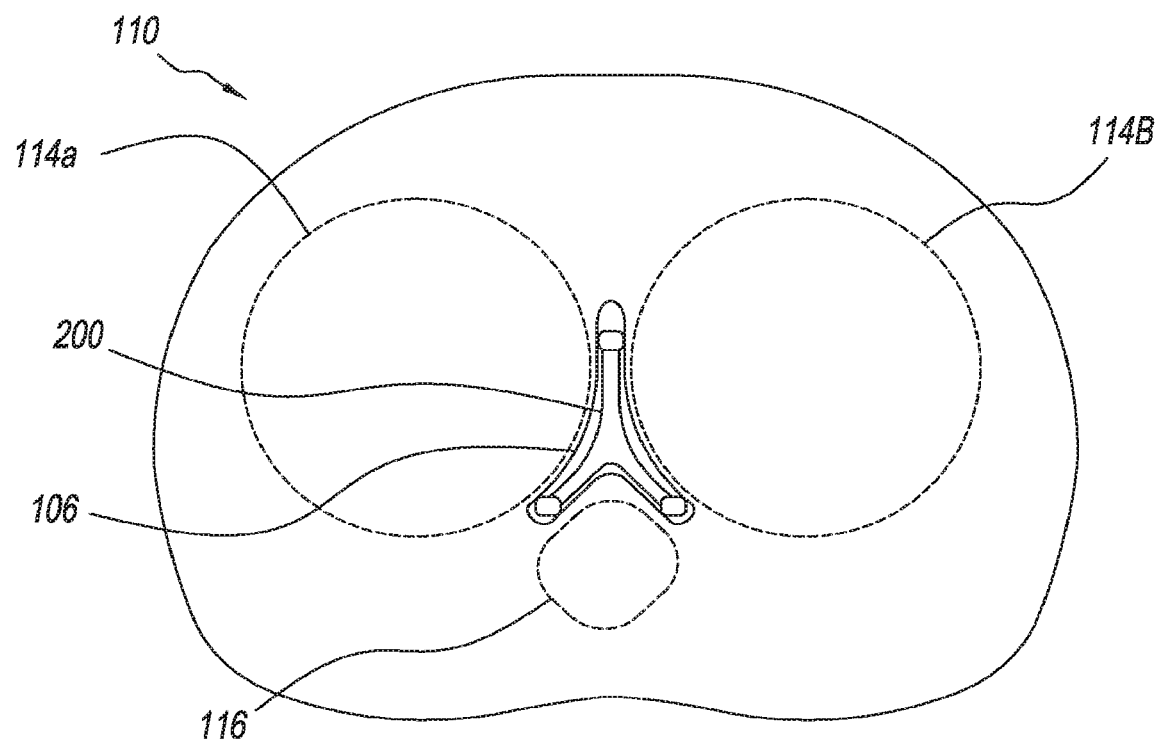
FIG. 3A schematically illustrates the exemplary embodiment of the stressed prostatic implant shown in FIG. 2D immediately following insertion thereof into the (BPH exhibiting) anatomical region portion shown in FIG. 1C, highlighting exemplary (insertion stage) positioning and configuration of the stressed prostatic implant relative to the (compressed) prostatic urethra and prostate lobes [dashed line circles]

FIG. 3A schematically illustrates the exemplary embodiment of the stressed prostatic implant 200 shown in FIG. 2D immediately following insertion thereof into the (BPH exhibiting) anatomical region portion 110 shown in FIG. 1C. FIG. 3A highlights exemplary (insertion stage) positioning and configuration of the stressed prostatic implant 200 relative to the compressed prostatic urethra 106 and the prostatic lobes (left and right prostatic lateral lobes 114a and 114b, respectively, and prostatic medial lobe 116).

Figure 3B:
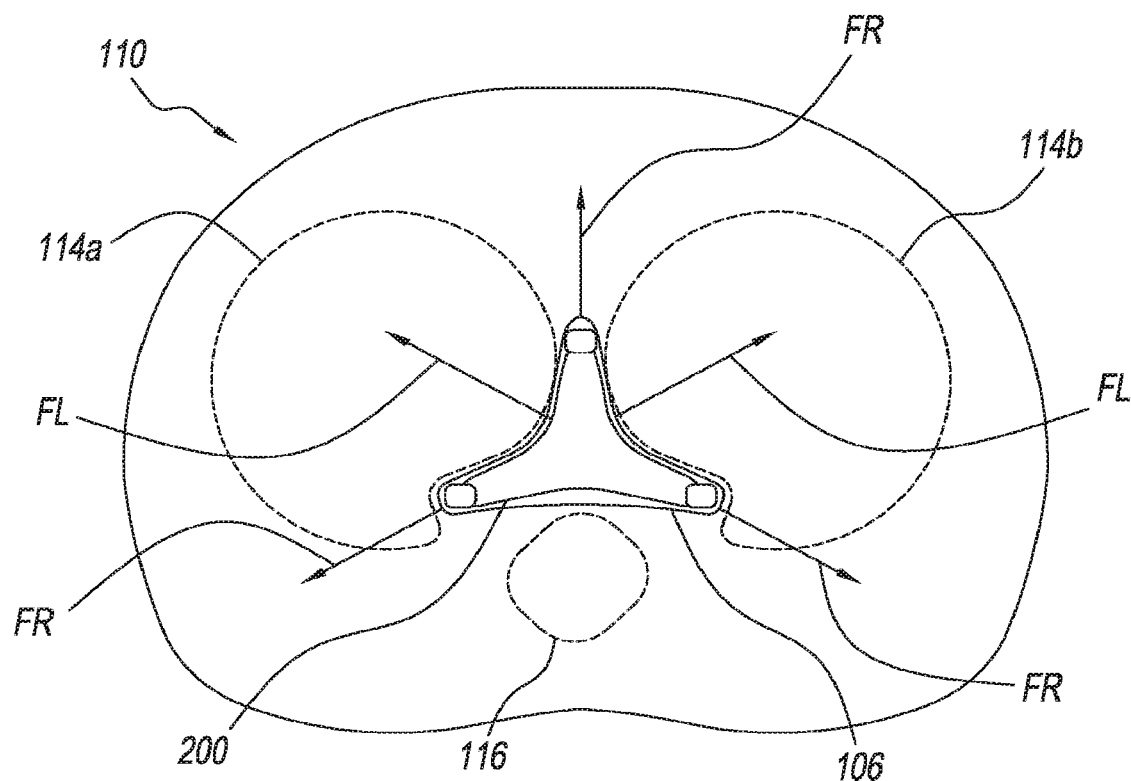
FIG. 3B schematically illustrates the exemplary prostatic implant shown in FIG. 3A following release thereof inside the (BPH exhibiting) anatomical region portion shown in FIG. 1C, highlighting exemplary (release stage) positioning and configuration of the non-stressed prostatic implant relative to the (compressed) prostatic urethra and prostate lobes [dashed line circles]

FIG. 3B schematically illustrates the exemplary prostatic implant 200 shown in FIG. 3A following release thereof inside the (BPH exhibiting) anatomical region portion 110. FIG. 3B highlights exemplary (release stage) positioning and configuration of the prostatic implant 200 now being 'less-stressed' (e.g., by undergoing elastic deformation under smaller external stresses, resulting in less strain thereof) relative to the compressed prostatic urethra 106 and the prostatic lobes. Structural change of the prostatic implant 200 (in changing from a stressed configuration of FIG. 3A to a non-stressed configuration of FIG. 3B) is accompanied by radially directed forces FR outwardly originating from the distal and proximal retractors 202 and 206, respectively, in a manner such that the prostatic implant 200 laterally expands and changes from a stressed configuration (FIG. 3A) to a partially- or less-stressed configuration (FIG. 3B). This, at least, effects anchoring of implant 200 within the particular anatomy of the BPH prostatic urethra, which prevents dislodgement or migration thereof in cranial or caudal directions, as well as rotational movement. Moreover, such structural change of the prostatic implant 200, via the radially directed forces FR outwardly originating from the distal and proximal retractors 202 and 206, respectively, translates into laterally directed pushing or pressure forces FL exerted by the distal and proximal retractors 202 and 206, respectively, upon those portions of the prostatic lobes (left and right prostatic lateral lobes 114a and 114b, respectively, and prostatic medial lobe 116) in contact with the prostatic implant 200, in general, and in contact with the distal and proximal retractors 202 and 206, respectively, in particular.

Additional exemplary and optional technical features, characteristics, and properties of an implant, for example, prostatic implant 200, for retracting or/and supporting periurethral tissue enclosing to a prostatic urethra along a length of prostate lobes, according to some embodiments of the invention, are illustratively described as follows.

In exemplary embodiments, the distal retractor 202 or/and the proximal retractor 206 are in a form of a pair of first and second curved wing-like structures connected to spine member 210 via interconnecting members 217, and symmetrically opposing each other relative to the spinal longitudinal axis 212. In exemplary embodiments, each interconnecting member includes at least one elastic portion, for example, elastic portion 218, adjoining the spine member 210, such that the elastic portion is non-stressed when the first curved wing-like structure in the pair is pivotally positioned centrally away from the second curved wing-like structure in the pair about the spinal longitudinal axis 212, so as to form a predetermined maximal elongated edge member spanning angle. In exemplary embodiments, each elastic portion adjoining the spine member 210 exhibits an increase in stress (e.g., bending or/and compression) when subjected to a moment of force that pivotally shifts the first curved wing-like structure towards the second curved wing-like structure about the spinal longitudinal axis 212.

In exemplary embodiments, the prostatic implant 200 additionally includes at least one tissue support member extending between a first elongated edge member, for example, first elongated edge member 214, and the spinal longitudinal axis 212, and at least one other tissue support member extending between a second elongated edge member, for example, second elongated edge member 216, and the spinal longitudinal axis 212. In exemplary embodiments, each tissue support member is sized and configured for supporting a portion of a prostatic lateral lobe, for example, left prostatic lateral lobe 114a or right prostatic lateral lobe 114b, when the spine member 210 engages an anterior interlobar groove, for example, anterior interlobar groove 118, that extends between left and right prostatic lateral lobes 114a and 114b, respectively, and when the first and second elongated edge members 214 and 216, respectively, engage corresponding posterolateral interlobar grooves, for example, left and right posterolateral interlobar grooves 120a and 120b, respectively.

In exemplary embodiments, the spine member 210 has a length being equal to or less than length of the anterior interlobar groove 118 or/and substantially less than the length of each of the first and second elongated edge members 214 and 216, respectively. In exemplary embodiments, the first elongated edge member 214 is sized for positioning in the left posterolateral interlobar groove 120a that extends between the left prostatic lateral lobe 114a and the prostatic medial lobe 116, and the second elongated edge member 216 is sized for positioning in the right posterolateral interlobar groove 120b that extends between the right prostatic lateral lobe 114b and the prostatic medial lobe 116.

Figure 4A:
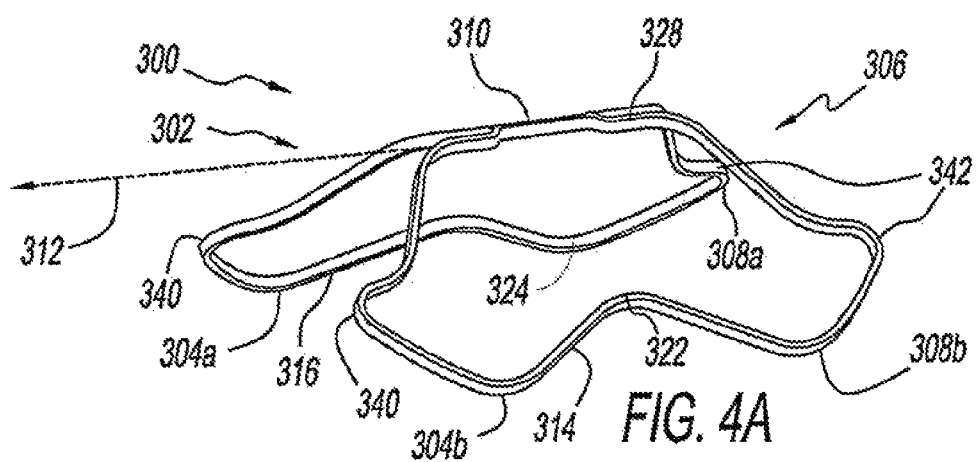
FIG. 4A-4C schematically illustrate perspective, front, and top views, respectively, of another exemplary embodiment of an implant for retracting or/and supporting periurethral tissue enclosing a prostatic urethra along a length of prostate lobes, highlighting some prostatic implant components, in accordance with some embodiments of the invention.
Figure 4B:
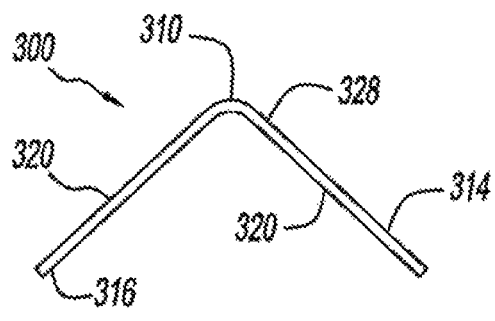
Figure 4C:
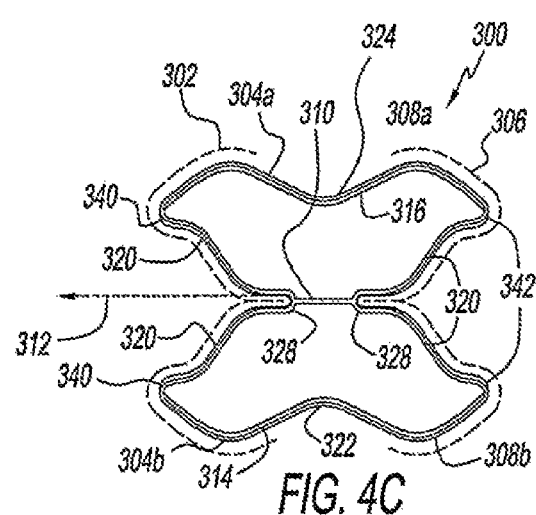

FIGS. 4A-4C schematically illustrate a perspective view, a frontal view, and a top view, respectively, of another exemplary embodiment of an implant (indicated as, and referred to by, reference to number 300) for retracting or/and supporting periurethral tissue enclosing a prostatic urethra along a length of prostate lobes, highlighting some prostatic implant components. According to such an exemplary embodiment, exemplary prostatic implant 300, in a non-limiting manner, includes: a distal retractor 302 incorporating a first craniolateral corner 304a and a second craniolateral corner 304b, and a proximal retractor 306 incorporating a first caudolateral corner 308a and a second caudolateral corner 308b.

In exemplary embodiments, the prostatic implant 300 additionally includes an elongated spine member 310. In such exemplary embodiments, the distal retractor 302 is connected to, or integrally formed as a single structure with, the proximal retractor 306, via the elongated spine member 310 extending along a spinal longitudinal axis 312 or/and a plurality of elongated edge members, for example, first and second elongated edge members, 314 and 316, respectively.

In exemplary embodiments, the distal retractor 302 and the proximal retractor 306 are independently actuatable. Specifically, actuation (i.e., movement or/and change in configuration, shape or form, or/and position) of the distal retractor 302 is at least partly, or entirely, independent of actuation (movement or/and change in configuration, shape or form, or/and position) of the proximal retractor 306, and vice versa. In exemplary embodiments, such actuation may be in the form of an 'indirect' actuation, for example, by indirectly actuating the distal retractor 302 or/and the proximal retractor 306 using external means. In such exemplary embodiments, the indirect external means may include or involve using an implant delivery system, for example, in a form of an operative combination of an implant manipulator and a compression sleeve, for example, implant manipulator 410 and compression sleeve 404 illustratively described hereinbelow and shown in FIGS. 7A-7C, and 8A-8L, in the context of an exemplary embodiment of a prostatic implant system).

Independent actuation of the distal retractor 302 and the proximal retractor 306 of prostatic implant 300 is analogous to that exemplified for the distal retractor 202 and the proximal retractor 206 of prostatic implant 200 shown in FIGS. 2B and 2C. Thus, similar to that shown in FIG. 2B, for the exemplary prostatic implant 300 shown in FIGS. 4A-4C, the implant distal retractor 302 may exhibit a non-stressed configuration, while the implant proximal retractor 306 may exhibit a stressed configuration. Additionally, similar to that shown in FIG. 2C, for the exemplary prostatic implant 300, both the implant distal retractor 302 and the proximal retractor 306 may exhibit a non-stressed configuration.

Accordingly, exemplary prostatic implant 300 is capable of undergoing a structural change in a manner whereby, for example, the distal retractor 302 is not actuated and remains in a non-stressed configuration (analogous to that shown in both FIGS. 2B and 2C), whereas the proximal retractor 306 is actuated and changes or shifts from a stressed configuration (analogous to that shown in FIG. 2B) to a non-stressed configuration (analogous to that shown in FIG. 2C). Such actuation, in the form of configurational change or shift, of the proximal retractor 306 is independent of non-actuation of the distal retractor 302.

Preceding illustratively described structural change of the exemplary prostatic implant 300 shown in FIGS. 4A-4C is analogous to that illustratively described hereinabove regarding structural change of the exemplary prostatic implant 200 as shown in FIGS. 2D-2E. Accordingly, such structural change of the exemplary prostatic implant 300 in changing from a stressed (e.g., compressed) configuration (analogous to that shown in FIG. 2D) to a non-stressed (e.g., non-compressed) configuration (analogous to that shown in FIG. 2E), is accompanied by radially directed forces outwardly originating from the distal and proximal retractors 302 and 306, respectively, in a manner such that the prostatic implant 300 laterally expands and changes from a stressed configuration to a non-stressed configuration.

Exemplary implementation and use of the prostatic implant 300, for retracting or/and supporting periurethral tissue enclosing a prostatic urethra along a length of prostate lobes, according to some embodiments of the invention, are analogous to that illustratively described hereinabove regarding the exemplary prostatic implant 200 as shown in FIGS. 3A and 3B.

Accordingly, in a manner analogous to that shown in FIG. 3A, prostatic implant 300, when in a stressed (e.g., compressed or folded) configuration, may be inserted into the (BPH exhibiting) anatomical region portion 110 shown in FIG. 1C. For example, with reference made to FIG. 3A, exemplary prostatic implant 200 can be substituted with exemplary prostatic implant 300, for highlighting exemplary (insertion stage) positioning and configuration of the stressed (compressed or folded) prostatic implant 300 relative to the (compressed) prostatic urethra 106 and the prostatic lobes (left and right prostatic lateral lobes 114a and 114b, respectively, and prostatic medial lobe 116).

Additionally, for example, with reference made to FIG. 3B, exemplary prostatic implant 200 can be substituted with exemplary prostatic implant 300, for schematically illustrating the stressed (compressed or folded) configuration of exemplary prostatic implant 300 following release thereof inside the (BPH exhibiting) anatomical region portion 110. According to such analogy, FIG. 3B, prostatic implant 200 being replaced by prostatic implant 300, would then highlight exemplary (release or unfolding stage) positioning and configuration of the 'less-stressed' (partially or entirely unfolded) prostatic implant 300 relative to the 'more-stressed' prostatic urethra 106 and the prostatic lobes. Structural change of the prostatic implant 300 (in changing from the stressed (compressed or folded) configuration to the non-stressed (partially or entirely unfolded) configuration is accompanied by radially directed forces outwardly originating from the distal and proximal retractors 302 and 306, respectively, in a manner such that the prostatic implant 300 laterally expands (i.e., unfolds) and changes from a stressed (compressed or folded) configuration to a non-stressed (partially or entirely unfolded) configuration. Moreover, such structural change of the prostatic implant 300, via the radially directed forces outwardly originating from the distal and proximal retractors 302 and 306, respectively, translates into laterally directed pushing or pressure forces exerted by the distal and proximal retractors 302 and 306, respectively, upon those portions of the prostatic lobes (left and right prostatic lateral lobes 114a and 114b, respectively, and prostatic medial lobe 116) in contact with the prostatic implant, in general, and in contact with the distal and proximal retractors 302 and 306, respectively, in particular.

Reference is again made to FIG. 4A, schematically illustrating a perspective view of exemplary prostatic implant 300, for retracting or/and supporting periurethral tissue enclosing a prostatic urethra along a length of prostate lobes, highlighting some prostatic implant components. According to such an alternative exemplary embodiment, exemplary prostatic implant 300, in a non-limiting manner, includes: an elongated spine member 310 having a spinal longitudinal axis 312, and, a first elongated edge member 314 and a second elongated edge member 316 symmetrically opposing each other relative to the spinal longitudinal axis 312. Therein, each of the first and second elongated edge members 314 and 316, respectively, is interconnected to the spine member 310 via at least one interconnecting member, for example, interconnecting member 320.

According to this exemplary embodiment, exemplary prostatic implant 300 additionally includes at least one tissue support member, for example, first tissue support member 322, extending between the first elongated edge member 314 and the spinal longitudinal axis 312, and at least one other tissue support member, for example, second tissue support member 324, extending between the second elongated edge member 316 and the spinal longitudinal axis 312. Therein, each of the tissue support members, for example, each of the first and second tissue support members 322 and 324, respectively, is sized and configured for supporting a portion of a prostatic lateral lobe (for example, left or right prostatic lateral lobe 114a or 114b, respectively, shown in FIGS. 1C, 3A, 3B) when the spine member 310 engages an anterior interlobar groove (for example, anterior interlobar groove 118 shown in FIGS. 1C, 3A, 3B) that extends between prostatic lateral lobes, and when the first and second elongated edge members 314 and 316, respectively, engage corresponding posterolateral interlobar grooves (for example, left and right posterolateral interlobar grooves 120a and 120b, shown in FIGS. 1C, 3A, 3B).

Additional exemplary and optional technical features, characteristics, and properties of an implant, for example, prostatic implant 300, for retracting or/and supporting periurethral tissue enclosing a prostatic urethra along a length of prostate lobes, according to some embodiments of the invention, are illustratively described as follows.

In exemplary embodiments, the spine member 310 has a length being equal to or less than length of the anterior interlobar groove 118 or/and substantially less than the length of each of the first and second elongated edge members 314 and 316, respectively. In exemplary embodiments, the first elongated edge member 314 is sized for positioning in the left posterolateral interlobar groove 120a that extends between the left prostatic lateral lobe 114a and the prostatic medial lobe 116, and the second elongated edge member 316 is sized for positioning in the right posterolateral interlobar groove 120b that extends between the right prostatic lateral lobe 114b and the prostatic medial lobe 116.

In exemplary embodiments, the prostatic implant 300 is configured to anchor the anterior interlobar groove 118, and, the left and right posterolateral interlobar grooves 120a and 120b, respectively, by continuously exerting a radially directed pushing force thereupon, within a range of between about 100 grams and about 1,000 grams, so as to prevent or minimize axial or/and rotational movement of the anchored anterior interlobar groove 118, and, the posterolateral interlobar grooves 120a and 120b. In exemplary embodiments, the prostatic implant 300 is configured to anchor the anterior interlobar groove 118, and, the left and right posterolateral interlobar grooves 120a and 120b, respectively, by continuously exerting a radially directed pushing force thereupon, so as to increase distance separating superior portions of the interlobar grooves and increase distance separating left and right inferior portions of the interlobar grooves, or/and to maintain a distance of at least 2 mm between the prostatic lateral lobes, by exerting lateral forces thereupon within a range of between about 100 grams and about 1,000 grams.

In exemplary embodiments, implant 300 is shown in FIG. 4A as fully unfolded and fully unstressed, having its double wings-like structure fully opened and expanded laterally. In exemplary embodiments, each of the interconnecting members, for example, interconnecting member 320, includes at least one elastic portion, for example, elastic portion 328, adjoining the spine member 310, such that the elastic portion 328 is non-stressed when the first and second elongated edge members 314 and 316, respectively, are pivotally positioned centrally away from each other about the spinal longitudinal axis 312, so as to form a predetermined maximal spanning angle between opposing interconnecting members. In exemplary embodiments, the predetermined maximal spanning angle is within a range of between about 60° and about 140°. In exemplary embodiments, each elastic portion, for example, elastic portion 328, adjoining the spine member 310 exhibits an increase in stress (compression) when subjected to a moment of force that pivotally shifts the first and second elongated edge members 314 and 316, respectively, towards each other about the spinal longitudinal axis 312.

In exemplary embodiments, the first and second edge members 314 and 316, respectively, are configured to approach each other so as to form an elongated edge member spanning angle being equal to or greater than about 60° degrees. In such exemplary embodiments, each of the first and second elongated edge members 314 and 316, respectively, or/and each of the first and second tissue support members 322 and 324, respectively, exerts a total lateral pressing force upon a corresponding prostatic lateral lobe. In exemplary embodiments, the total lateral pressing force is in a range of between about 100 grams and about 1,000 grams.

In exemplary embodiments, each of the first and second tissue support members 322 and 324, respectively, is configured as a curvilinear portion of the first elongated edge member 314 or/and the second elongated edge member 316 protruding towards the spinal longitudinal axis 312. In exemplary embodiments, each of the first and second tissue support members 322 and 324, respectively, is configured as a curvilinear portion of the first elongated edge member 314 or/and the second elongated edge member 316 that protrudes laterally outwardly from an area encompassed by the first elongated edge member 314 or/and the second elongated edge member 316 and the spine member 310.

FIG. 4C schematically illustrates a top view of the exemplary prostatic implant 300 shown in FIG. 4A, in a fully non-stressed configuration, highlighting a cranial-nose portion 340 thereof and a caudal-nose portion 342 thereof.

In exemplary embodiments, for example, as shown in FIG. 4C, at least one of the first and second elongated edge members 314 and 316, respectively, has a cranial-nose portion, for example, cranial-nose portion 340, shaped and configured for resting against a ledge imposed by a urinary bladder neck segment adjacent the prostatic urethra (e.g., 108 in FIG. 1A), so as to prevent cranial dislodgement of the prostatic implant 300 into the urinary bladder (e.g., 102 in FIG. 1A), when the spine member 310 engages an anterior interlobar groove (e.g., 118 in FIG. 1C) that extends between the prostatic lateral lobes (e.g., 114a and 114b in FIGS. 1C, 3A, 3B), and when the first and second elongated edge members 314 and 316, respectively, engage corresponding posterolateral interlobar grooves (e.g., 120a and 120b in FIGS. 1C, 3A, 3B). In such exemplary embodiments, the cranial-nose portion 340 is "L" shaped.

In exemplary embodiments, for example, as also shown in FIG. 4C, at least one of the first and second elongated edge members 314 and 316, respectively, has a caudal-nose portion, for example, caudal-nose portion 342, shaped and configured for resting against a narrowing imposed by the external urethral sphincter adjacent to the verumontanum of the prostatic urethra, so as to prevent caudal migration of the prostatic implant 300 through the external sphincter and into the bulbar urethra, when the spine member 302 engages an anterior interlobar groove (e.g., 118 in FIG. 1C) that extends between the prostatic lateral lobes (e.g., 114a and 114b in FIGS. 1C, 3A, 3B), and when the first and second elongated edge members 314 and 316, respectively, engage corresponding posterolateral interlobar grooves (e.g., 120a and 120b in FIGS. 1C, 3A, 3B). In such exemplary embodiments, the caudal-nose portion 342 is "L" shaped.

Figure 5:
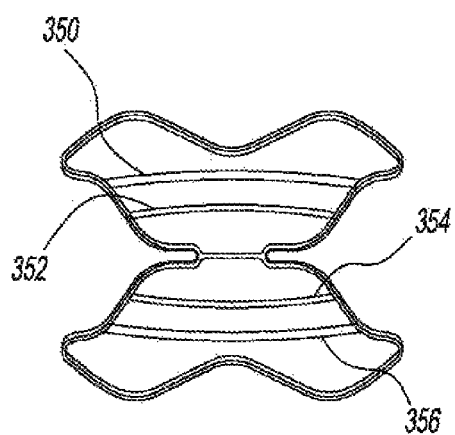
FIG. 5 schematically illustrates the exemplary prostatic implant shown in FIG. 4C, highlighting inclusion therein of a plurality of exemplary tissue support members, each configured as a rib or rib-type member, in accordance with some embodiments of the invention.

FIG. 5 schematically illustrates the exemplary prostatic implant shown in FIG. 4C, highlighting inclusion therein of a plurality of exemplary tissue support members 350, 352, 354, and 356, where each such tissue support member is configured as a rib or rib-type member.

Figure 6:
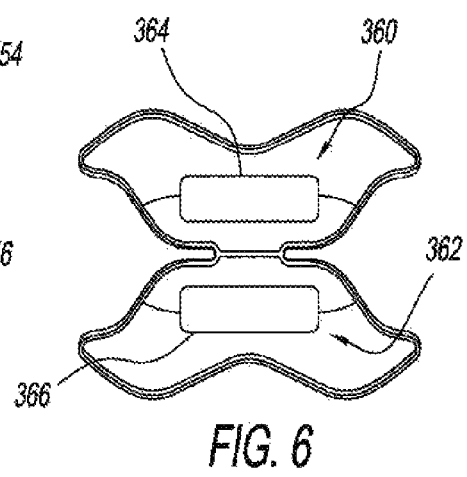
FIG. 6 schematically illustrates the exemplary prostatic implant shown in FIG. 4C, highlighting inclusion therein of a pair of exemplary tissue support members with each member including a tissue contacting surface, in accordance with some embodiments of the invention.

FIG. 6 schematically illustrates the exemplary prostatic implant shown in FIG. 4C, highlighting inclusion therein of a pair of exemplary first and second tissue support members 360 and 362, with each such tissue support member including a tissue contacting surface, for example, first and second tissue contacting surfaces 364 and 366, respectively.

In exemplary embodiments, at least one of the tissue support members, for example, at least one of the first and second tissue support members 322 and 324, respectively, or/and rib or rib-type tissue support member 318, includes a tissue contacting surface, such as tissue contacting surface 364 or 366, sized or/and shaped according to dimensions of a portion of a prostatic lateral lobe (for example, left or right prostatic lateral lobe 114a or 114b, respectively, shown in FIGS. 1C, 3A, 3B).

An aspect of some embodiments of the present invention is a system (herein, also referred to as a prostatic implant system) for retracting or/and supporting periurethral tissue enclosing a prostatic urethra along a length of prostate lobes. In exemplary embodiments, the prostatic implant system, in a non-limiting manner, includes: an implant (prostatic implant), and an implant (prostatic implant) manipulator detachably connected to the implant (prostatic implant). Therein, the prostatic implant includes a plurality of elongated edge members interconnected in a form of a collapsible-expandable frame expandable to retract or/and support periurethral tissue by exerting pushing forces upon interlobar grooves located along the prostatic urethra. Additionally, therein, a first one of the elongated edge members includes a first craniolateral corner and a first caudolateral corner, and a second one of the elongated edge members includes a second craniolateral corner opposing the first craniolateral corner and a second caudolateral corner opposing the first caudolateral corner. In such exemplary embodiments, the implant manipulator is configured to manipulate and force the implant first and second caudolateral corners into close proximity with each other.

Any of the hereinabove illustratively described exemplary embodiments of an implant (prostatic implant), such as exemplary prostatic implant 200 or exemplary prostatic implant 300, for retracting or/and supporting periurethral tissue enclosing a prostatic urethra along a length of prostate lobes may be included as part of, and used for implementing, the herein disclosed exemplary embodiments of a system (prostatic implant system) for retracting or/and supporting periurethral tissue enclosing a prostatic urethra along a length of prostate lobes.

Figure 7A:
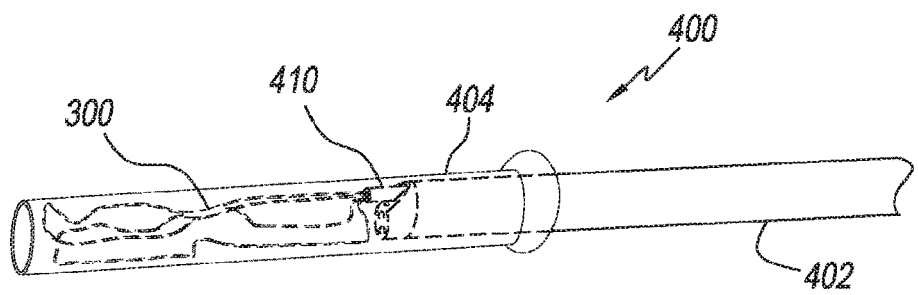
FIG. 7A schematically illustrates an exemplary embodiment of a system for retracting or/and supporting periurethral tissue enclosing a prostatic urethra along a length of prostate lobes, highlighting some system components, wherein an exemplary prostatic implant (such as that shown in FIGS. 4A and 4C), in a stressed configuration and operatively connected to an exemplary cystoscope, is entirely held within an exemplary compression sleeve by an implant manipulator, in accordance with some embodiments of the invention.

For example, reference is made to FIG. 7A which schematically illustrates an exemplary embodiment of a system (prostatic implant system), indicated as, and referred to by, reference number 400, for retracting or/and supporting periurethral tissue enclosing a prostatic urethra along a length of prostate lobes, highlighting some system components. Therein, an exemplary prostatic implant (such as prostatic implant 300 shown in FIGS. 4A and 4C), in a stressed (e.g., bent, contracted or/and compressed, folded type) configuration and operatively connected to the distal end of an exemplary cystoscope 402, is entirely held within an exemplary compression sleeve 404 by an implant manipulator 410 (also described below and shown in more details in FIGS. 8E-8G, and 8M).

With reference to FIG. 7A, and FIGS. 4A-4C, exemplary prostatic implant system 400, in a non-limiting manner, includes: an implant (prostatic implant) 300, and an implant (prostatic implant) manipulator 410 detachably connected to the prostatic implant 300. Therein, the prostatic implant 300 includes a plurality of elongated edge members, for example, first and second elongated edge members 314 and 316, respectively, interconnected in a form of a collapsible-expandable frame expandable to retract or/and support periurethral tissue by exerting pushing forces upon interlobar grooves located along the prostatic urethra (e.g., as illustratively described hereinabove with reference to FIGS. 1A-1C, and 3A-3B). Additionally, therein, the first elongated edge member 314 includes a first craniolateral corner 304a and a first caudolateral corner 308a, and the second elongated edge member 316 includes a second craniolateral corner 304b opposing the first craniolateral corner 304a and a second caudolateral corner 308b opposing the first caudolateral corner 308a. In such exemplary embodiments, the implant manipulator 410 (e.g., FIGS. 8E-8G) is configured to manipulate and force the prostatic implant first and second caudolateral corners 308a and 308b, respectively, into close proximity with each other.

Additional exemplary and optional technical features, characteristics, and properties, as well as exemplary implementation and use, of a system, for example, prostatic implant system 400, for retracting or/and supporting periurethral tissue enclosing a prostatic urethra along a length of prostate lobes, according to some embodiments of the invention, are illustratively described as follows.

Figure 7B:
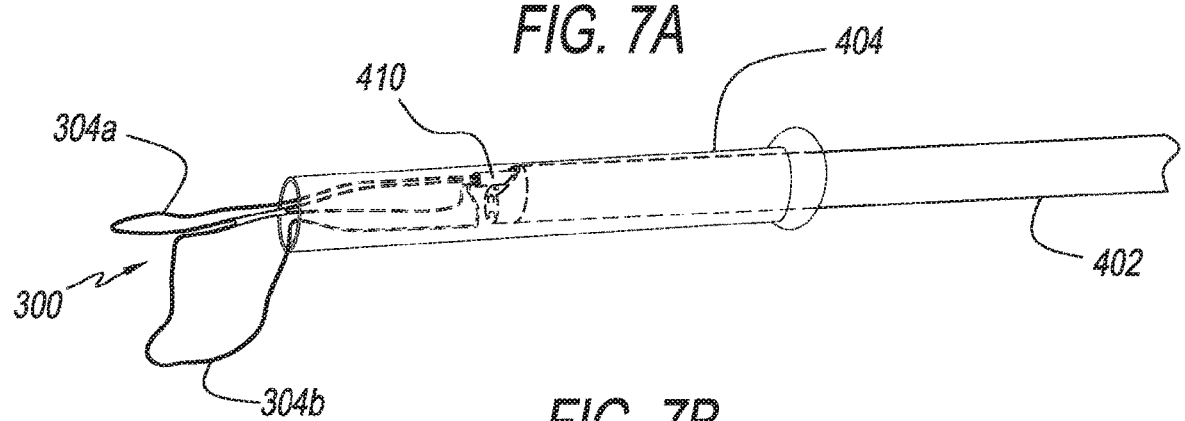
FIGS. 7B-7C schematically illustrate exemplary embodiments of the system shown in FIG. 7A, highlighting progressive (sequential) stages of operation thereof, wherein the exemplary prostatic implant is deployed via progressively (sequentially) being pushed out of the compression sleeve by the implant manipulator, in accordance with some embodiments of the invention.
Figure 7C:
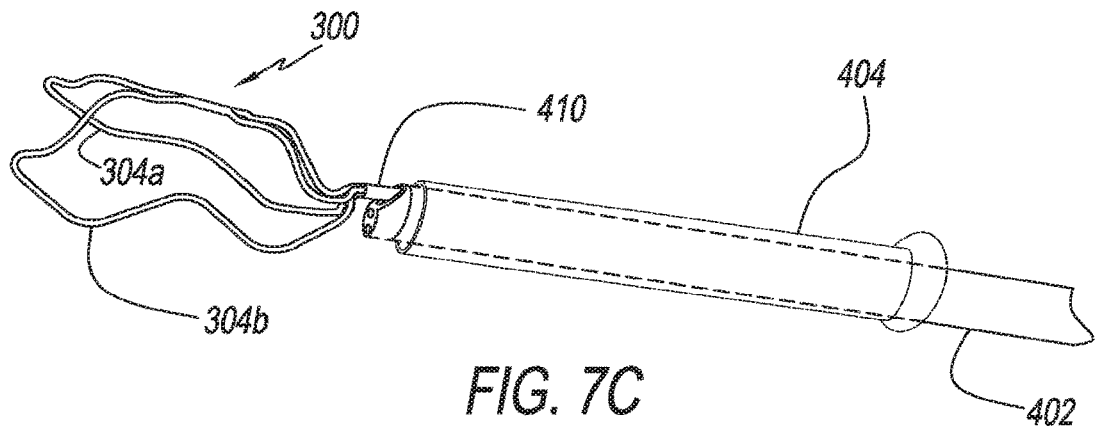
Figure 7D:
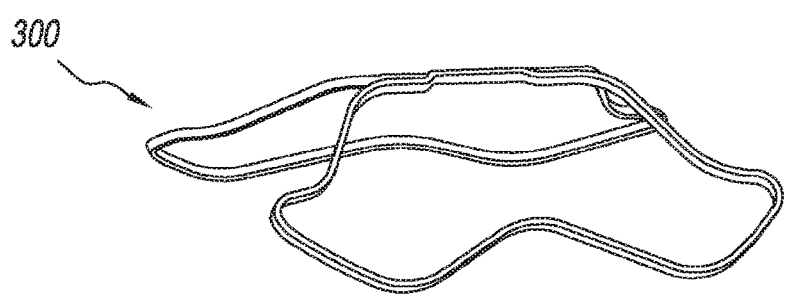
FIG. 7D schematically illustrates the exemplary prostatic implant shown in FIGS. 7A-7C, following deployment by the system, in a 'stand-alone' non-stressed expanded configuration after exiting the compression sleeve and detachment from the implant manipulator, in accordance with some embodiments of the invention.

FIGS. 7B-7C schematically illustrate exemplary embodiments of the prostatic implant system 400, highlighting progressive (sequential) stages of operation thereof, wherein the exemplary prostatic implant 300 is deployed via progressively (sequentially) being pushed out of the compression sleeve 404 by the implant manipulator 410, along with undergoing a type of unfolding of at least some of its structural members. At first (FIG. 7B), distal retractor 302 emerges and then immediately unfolds, at least partly, while the other part of implant 300 is held folded and compressed in compression sleeve 404; followed by (FIG. 7C) complete extraction of implant 300 from within compression sleeve 404, where implant 300 is unfolded at least partly along most or all its entire length. FIG. 7D schematically illustrates the exemplary prostatic implant 300, following deployment by the prostatic implant system 400, in a 'stand-alone' non-stressed, unfolded and expanded configuration after exiting the compression sleeve 404 and detachment from the implant manipulator 410.

In exemplary embodiments of prostatic implant system 400, the implant manipulator 410 (e.g., FIGS. 8E-8G) is configured for progressively (sequentially) changing the shape or form of the prostatic implant 300 according to different progressive or sequential implant deployment configurations, including at least one of the following.

A fully collapsed delivery configuration, whereby the implant first and second craniolateral corners 304a and 304b, respectively, are in close proximity with each other, and, the implant first and second caudolateral corners 308a and 308b, respectively, are in close proximity with each other, for example, as shown in FIG. 7A. In exemplary embodiments, such a fully collapsed delivery configuration of the prostatic implant 300 corresponds to a fully folded configuration, whereby at least some of the prostatic implant structural members are in a type of a fully folded form.

A partially collapsed positioning configuration, whereby the implant first and second craniolateral corners 304a and 304b, respectively, are distanced apart from each other, and, the implant first and second caudolateral corners 308a and 308b, respectively, are in close proximity with each other, for example, as shown in FIG. 7B. In exemplary embodiments, such a partially collapsed positioning configuration of the prostatic implant 300 corresponds to a partially folded/partially unfolded configuration, whereby at least some of the prostatic implant structural members are in a type of a partially folded form while at least some others of the prostatic implant structural members are in a type of a partially unfolded form. In exemplary embodiments, the partially collapsed positioning configuration includes the prostatic implant 300 having a frustum or cone-like shape whose distal-most diameter thereof is greater than the smallest cross-sectional dimension in a urinary bladder neck joining the prostatic urethra (e.g., 108 and 106, respectively, in FIG. 1A), and whose proximal-most diameter thereof is smaller than the smallest cross-sectional dimension in the urinary bladder neck.

An expanded deployed configuration, whereby the implant first and second craniolateral corners 304a and 304b, respectively, are distanced apart from each other, and, the implant first and second caudolateral corners 308a and 308b, respectively, are distanced apart from each other, for example, as shown in FIGS. 7C and 7D. In exemplary embodiments, such an expanded deployed configuration of the prostatic implant 300 corresponds to a fully unfolded configuration, whereby at least most, or all, of the prostatic implant structural members are in a type of a fully unfolded form.

In exemplary embodiments, the implant manipulator 410 (e.g., FIGS. 8E-8G), when connected to the prostatic implant 300, is configured for applying thereto at least one of rotational forces, pulling forces, and pushing forces. The implant manipulator 410 applies such forces to the prostatic implant 300 so as to facilitate and effect preceding illustratively described progressive (sequential) changing of the shape or form of the prostatic implant 300, according to the different progressive or sequential prostatic implant deployment configurations.

In exemplary embodiments, the implant manipulator 410 includes a tubular member, for example, tubular member 412, and a tether, for example, tether 414, releasably intertwined through both of the implant first and second caudolateral corners. In such exemplary embodiments, the implant manipulator 410 is configured for continuously or/and selectively pulling the prostatic implant 300 via an operator using the tether 414 against a distal end 416 of the tubular member 412.

Figure 8A:
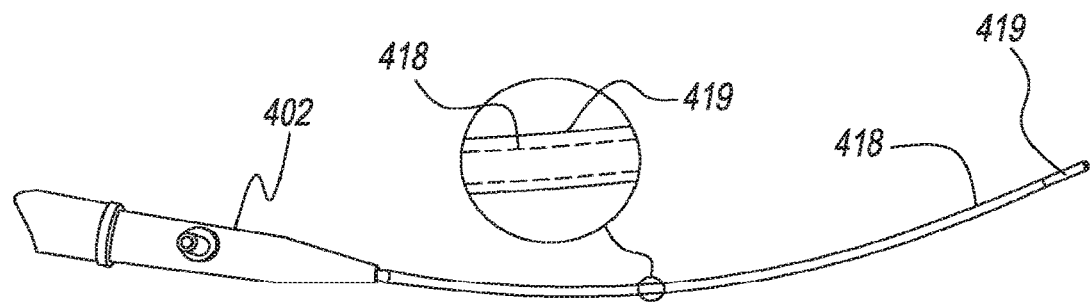
FIGS. 8A-8N schematically illustrate components and operation of an exemplary system (such as prostatic implant system 400 shown in FIGS. 7A-7C), including various stages of delivering and deploying an exemplary prostatic implant (such as prostatic implant 300 shown in FIGS. 4A, 4C, and 7D), for retracting or/and supporting periurethral tissue enclosing a prostatic urethra along a length of prostate lobes, in accordance with some embodiments of the invention.
Figure 8B:
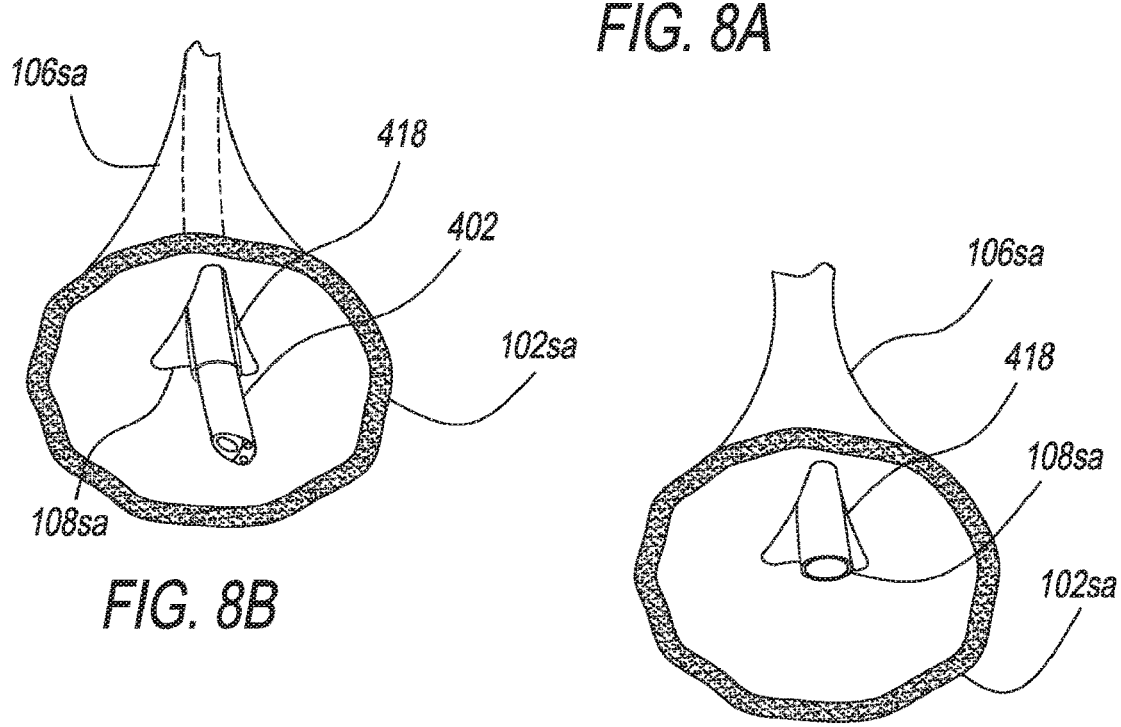
Figure 8C:
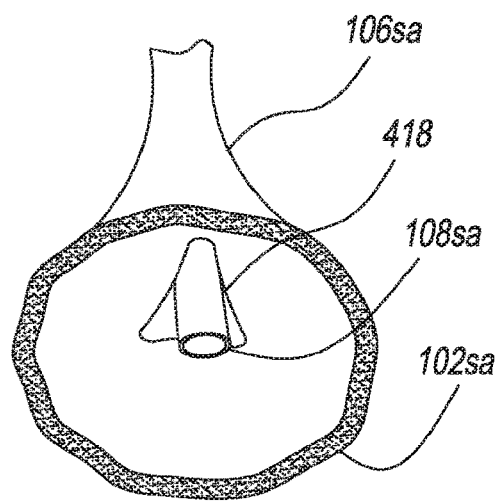

In exemplary embodiments, the prostatic implant system 400 additionally includes an over-sheath, for example, over-sheath 418 shown in FIGS. 8A-8C, sized for covering a length of the cystoscope 402 having a cystoscope lumen (e.g., as a type of 'working channel') dimensioned to restrain the prostatic implant 300 in the fully collapsed delivery configuration (e.g., FIG. 7A) via at least encircling the implant first and second craniolateral corners.

In such exemplary embodiments, the implant manipulator 410 is configured for manipulating and shifting the prostatic implant 300 within the over-sheath lumen between the fully collapsed (fully folded) delivery configuration (FIG. 7A) and the partially collapsed (and partially unfolded) positioning configuration (FIG. 7B). Such manipulating and shifting is effected by the implant manipulator 410 pushing or pulling the prostatic implant 300 relative to the over-sheath lumen until the implant first and second craniolateral corners 304a and 304b, respectively, are released from the implant manipulator over-sheath 418. Additionally, in such exemplary embodiments, the implant manipulator 410 is configured for manipulating and shifting the prostatic implant 300 between the partially collapsed (and partially unfolded) delivery configuration (FIG. 7B) and the expanded (and partially or fully unfolded along most/all implant 300 length) deployed configuration (FIGS. 7C, 7D). Such manipulating and shifting is effected by the implant manipulator 410 detaching from the prostatic implant 300 after release of the tether 414 from the implant first and second caudolateral corners 308a and 308b, respectively.

As stated above, any of the hereinabove illustratively described exemplary embodiments of an implant (prostatic implant) for retracting or/and supporting periurethral tissue enclosing a prostatic urethra along a length of prostate lobes may be included as part of, and used for implementing, the herein disclosed exemplary embodiments of a system (prostatic implant system) for retracting or/and supporting periurethral tissue enclosing a prostatic urethra along a length of prostate lobes.

Thus, with reference again made to FIG. 7A, and FIGS. 4A-4C, in exemplary embodiments of prostatic implant system 400, the prostatic implant 300 includes: an elongated spine member 310 having to a spinal longitudinal axis 312, and, first and second elongated edge members 314 and 316, respectively, symmetrically opposing each other relative to the spinal longitudinal axis 312, and interconnected to the spine member 310 via at least one interconnecting member 320. In such exemplary embodiments, the spine member 310 has a length being equal to or less than length of an anterior interlobar groove (e.g., 118 in FIGS. 1C, 3A, 3B) that extends between prostatic lateral lobes (e.g., left and right prostatic lateral lobes 114a and 114b, respectively, in FIGS. 1C, 3A, 3B), or/and substantially less than length of each of the first and second elongated edge members 314 and 316, respectively.

Further, in such exemplary embodiments of prostatic implant system 400 including prostatic implant 300, with additional reference made to FIGS. 1C, 3A, and 3B, the first elongated edge member 314 is sized for positioning in a left posterolateral interlobar groove 120a that extends between a left prostatic lateral lobe 114a and a prostatic medial lobe 116, and the second elongated edge member 316 is sized for positioning in a right posterolateral interlobar groove 120b that extends between a right prostatic lateral lobe 114b and the prostatic medial lobe 116.

Further, in such exemplary embodiments of prostatic implant system 400 including prostatic implant 300, at least one of the implant first and second craniolateral corners 304a and 304b, respectively, are shaped and configured for resting against a ledge imposed by the urinary bladder neck (e.g., 108) so as to prevent cranial dislodgement of the prostatic implant 300 into the urinary bladder (e.g., 102), when the spine member 310 engages an anterior interlobar groove (e.g., 118) that extends between prostatic lateral lobes (e.g., 114a and 114b), and when the first and second elongated edge members 314 and 316, respectively, engage corresponding posterolateral interlobar grooves (e.g., 120a and 120b).

Further, in such exemplary embodiments of prostatic implant system 400 including prostatic implant 300, at least one of the implant first and second caudolateral corners 308a and 308b, respectively, are shaped and configured for resting against a narrowing imposed by the external urethral sphincter adjacent the verumontanum of the prostatic urethra, so as to prevent caudal shift of the prostatic implant 300, when the spine member 310 engages an anterior interlobar groove (e.g., 118) that extends between prostatic lateral lobes (e.g., 114a and 114b), and when the first and second elongated edge members 314 and 316, respectively, engage corresponding posterolateral interlobar grooves (e.g., 120a and 120b). In such exemplary embodiments, each of the implant first and second caudolateral corners 308a and 308b, respectively, has a shape or form of a proximally directed apex, wherein the apex is formed by intersection of converging curved slopes of respective ones of the implant first and second caudolateral corners 308a and 308b, respectively.

An aspect of some embodiments of the present invention is a method (herein, also referred to as a prostatic implant method) for retracting or/and supporting periurethral tissue enclosing a prostatic urethra along a length of prostate lobes.

In exemplary embodiments, the prostatic implant method, in a non-limiting manner, includes:
  Providing an implant along a chosen length of the prostate lobes.
  Exerting continuous radially directed pushing forces upon the anterior interlobar groove between the prostate lobes, and upon at least one of the left and right posterolateral interlobar grooves between the prostate lobes, thereby anchoring the implant in-place.
  Exerting lateral pressing forces upon one or more of prostatic lateral lobes, thereby retracting or/and supporting the periurethral tissue.

In alternative exemplary embodiments, the prostatic implant method, in a non-limiting manner, includes:
  Providing an implant in a fully collapsed delivery configuration, the implant includes an independently actuatable distal retractor incorporating first and second craniolateral corners, and an independently actuatable proximal retractor incorporating first and second caudolateral corners, wherein the first and second craniolateral corners are in close proximity to each other, and, the first and second caudolateral corners are in close proximity to each other.
  Passing the implant in the fully collapsed delivery configuration, in a cranial direction in a subject's urethra, into the subject's urinary bladder.
  Expanding, optionally by unfolding, the distal retractor within inner boundaries of the urinary bladder.
  Positioning under vision the implant in the prostatic urethra along the length of the prostate lobes.
  Expanding, optionally by unfolding, the proximal retractor so as to effect changing the configuration of the implant from the fully collapsed (fully folded) delivery configuration, into an expanded (fully unfolded) deployed configuration wherein the first and second craniolateral corners are distanced apart from each other, and, the first and second caudolateral corners are distanced apart from each other. In some embodiments, unfolding or/and expanding of the implant is two-fold or/and multi-dimensional, for example by unfolding from a collapsed-thin form to larger, radially-expanded, size, in parallel to or followed by lateral expansion thereof.

Any of the hereinabove illustratively described exemplary embodiments of an implant (prostatic implant), such as exemplary prostatic implant 200 or exemplary prostatic implant 300, and any of the hereinabove illustratively described exemplary embodiments of a system (prostatic implant system), such as exemplary prostatic implant system 400, for retracting or/and supporting periurethral tissue enclosing a prostatic urethra along a length of prostate lobes, may be included as part of, and used for implementing, the herein disclosed exemplary embodiments of a method (prostatic implant method) for retracting or/and supporting periurethral tissue enclosing a prostatic urethra along a length of prostate lobes.

For example, reference is made to FIGS. 8A-8N which schematically illustrate various stages of delivering and deploying an exemplary prostatic implant, such as prostatic implant 300 illustratively described hereinabove and shown in FIGS. 4A, 4C, and 7D, for retracting or/and supporting periurethral tissue enclosing a prostatic urethra along a length of prostate lobes, using an exemplary system, such as prostatic implant system, such as prostatic implant system 400 illustratively described hereinabove and shown in FIGS. 7A-7C).

As shown in FIG. 8A, over-sheath 418 is sleeved over the longitudinal body 419 of a urological endoscope, particularly, a cystoscope (also known as a lithoscope), for example, cystoscope 402. Then some preliminary steps may be taken by an operator, such as a medical practitioner, in order to scan the treatment area or/and to measure patient-specific anatomical dimensions, optionally, in order to select an implant of proper size for a chosen result.

With reference to FIG. 8B, over-sheath 418, together with cystoscope 402, is then extended throughout the length of the prostatic urethra 106sa, where the cystoscope distal end 420 is provided adjacent to or inside of the urinary bladder 102sa. In FIG. 8B, the prostatic urethra 106sa, the urinary bladder 102sa, and the bladder neck 108sa, are drawn for illustrative purposes only, and, in a non-limiting manner, may be considered 'simulated analogs' of the corresponding bodily organs or parts, namely, prostatic urethra 106, urinary bladder 102, and bladder neck 108, schematically shown in FIGS. 1A-1C.

Figure 8D:
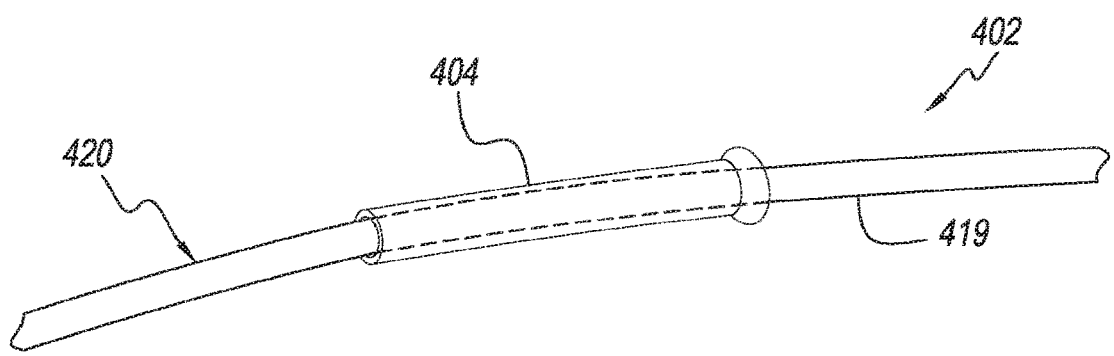

Cystoscope 402 is removed from the prostatic urethra 106sa while, optionally, keeping over-sheath 418 in place (as shown in FIG. 8C). Optionally, compression sleeve 404 is then loaded over cystoscope outer periphery 420 (as shown in FIG. 8D), in preparation of loading prostatic implant 300 into the cystocope 402 and collapsing of the prostatic implant 300 using the compression sleeve 404.

In order to collapse (e.g., via folding) the prostatic implant 300 from being in a non-stressed fully opened configuration to being in a fully collapsed (fully folded) delivery configuration, and insert prostatic implant 300 into the working channel 422 of the cystoscope 402, a tether 414, is first intertwined (unless it is readily provided as such), optionally, releasably, through both the first and second craniolateral corners 304a and 304b, respectively, of distal retractor 302 of implant 300. First and second craniolateral corners are then urged the into close proximity to each other, so as to effect changing of the prostatic implant 300 into the partially collapsed (partially folded/partially unfolded) positioning configuration, by pulling tether 414 against the distal end 416 of the tubular member 412.

Figure 8E:
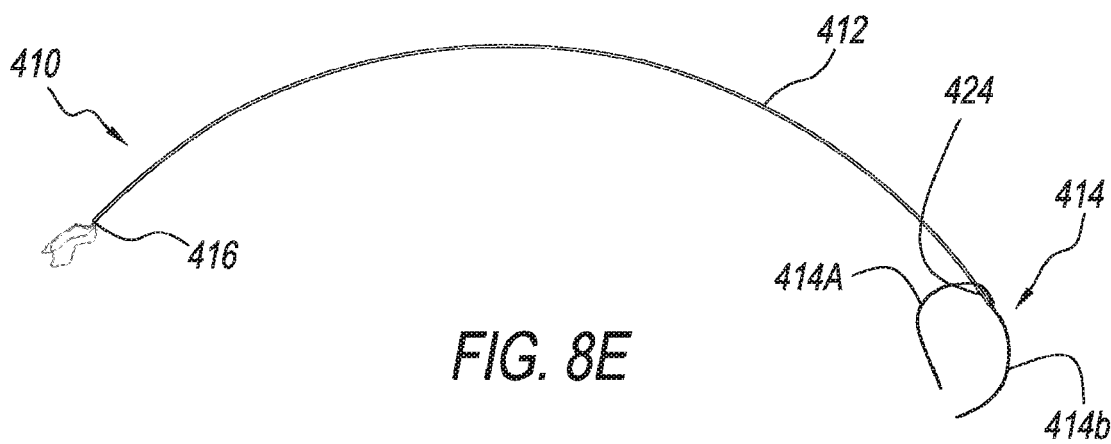

The implant manipulator 410, which can assist in exemplary subsequent steps, such as of implant delivery, positioning or/and activating, can be formed by threading tether 414 through the lumen of the tubular member 412, and optionally fixating proximal end (e.g., proximal both free ends 414a and 414b) of tether 414 relative to the proximal end 424 of tubular member 412. FIG. 8E demonstrates an exemplary formation of the implant manipulator 410 connected with the prostatic implant 300, also forcing it into the partially collapsed (partially folded/partially unfolded) positioning configuration.

Figure 8F:
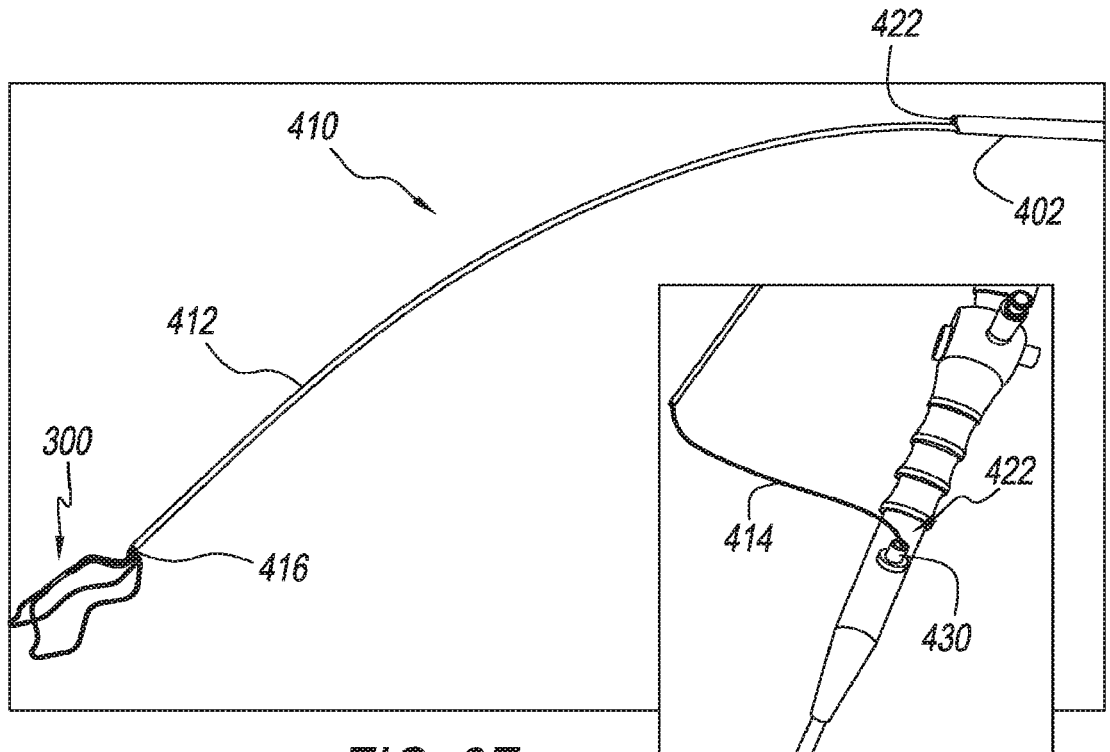
Figure 8G:
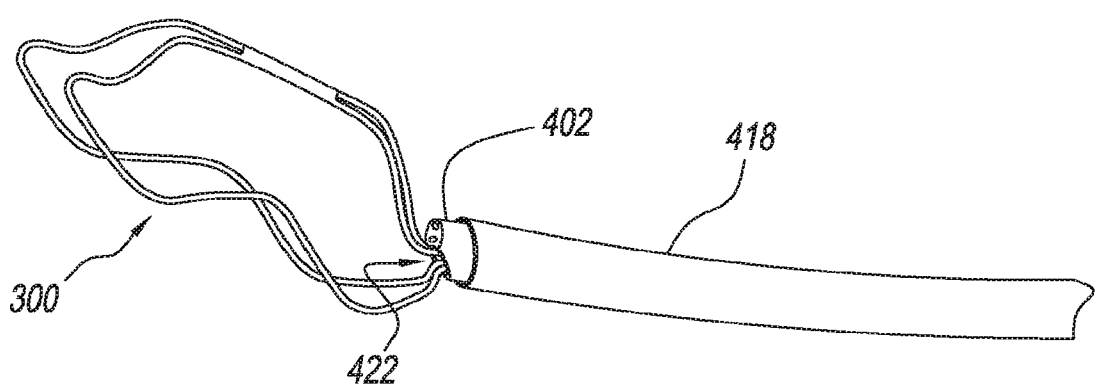

As shown in FIG. 8F, the implant manipulator 410, with the prostatic implant 300 connected thereto, are then loaded into a lumen (e.g., working channel 422) of the cystoscope 402. Optionally, the proximal end of the implant manipulator 410 is passed into the distal opening of the working channel 422 (FIG. 8F(i)), while the proximal end of the implant manipulator 410 is drawn from a proximal opening 430 of the working channel 422 (FIG. 8F(ii)). FIG. 8G shows the prostatic implant 300 in its partially collapsed (partially folded/partially unfolded) positioning configuration coupled to the cystoscope 402 using the implant manipulator 410 (not shown, fully inserted within working channel 422).

Figure 8H:
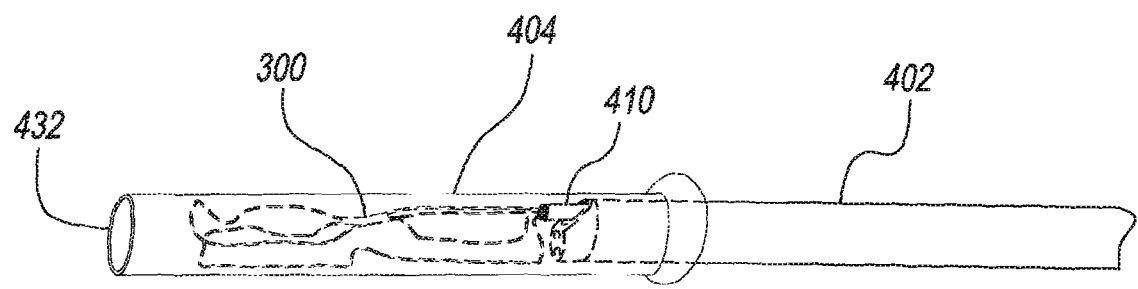
Figure 8I:
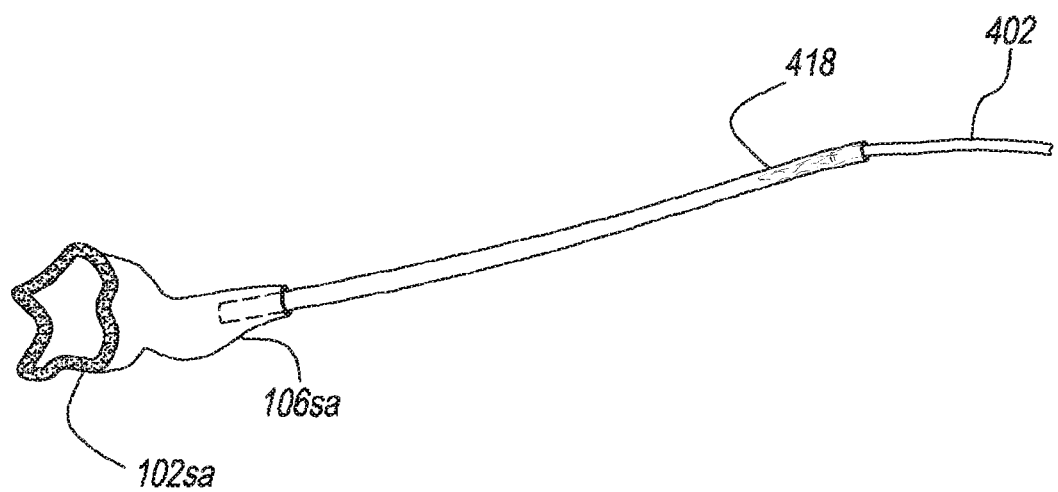
Figure 8J:
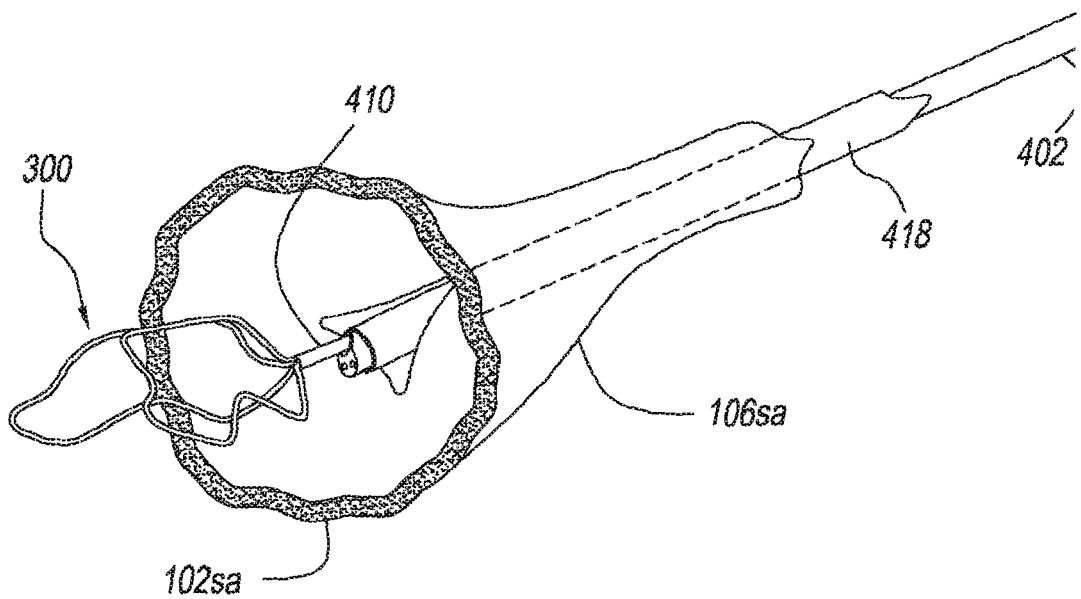

As shown in FIG. 8H, the prostatic implant 300 is then forced into a fully collapsed (fully folded) delivery configuration using the compression sleeve 402, by drawing the compression sleeve 404 over entire length of the prostatic implant 300. The compression sleeve 404 incorporates a lumen 432 sized for effecting changing of the configuration of the prostatic implant 300 from the partially collapsed (partially folded/partially unfolded) positioning configuration to the fully collapsed (fully folded) delivery configuration.

The prostatic implant 300 is then pushed distally through over-sheath 418 with the cystoscope 402 (FIG. 8I) and passed, still in its fully collapsed (fully folded) delivery configuration, in a cranial direction in the prostatic urethra 106sa, into the urinary bladder 102sa of the subject. Then, the prostatic implant distal retractor 302 is released from its restricting boundary, namely, the working channel 422 and the over-sheath 418, until at least the distal retractor 302, and, optionally, also the proximal retractor 306, protrudes in a cranial direction from the prostatic urethra 106sa (as shown, for example, in FIG. 8J). This may be effected by either pushing the prostatic implant 300, optionally relative to the over-sheath 418, or/and the cystoscope 402 further into the urinary bladder 102sa, or by holding the prostatic implant 300 in the urinary bladder 102sa, using the implant manipulator 410, while proximally pulling over-sheath 418 or/and the cystoscope 402.

Releasing the prostatic implant 300 should effect expansion of the distal retractor 302 within inner boundaries of the urinary bladder 102sa into the partially collapsed (partially folded/partially unfolded) positioning configuration, resulting in the first and second craniolateral corners 304a and 304b, respectively, being distanced apart from each other, and, the first and second caudolateral corners 308a and 308b, respectively, being kept in close proximity to each other.

Figure 8K:
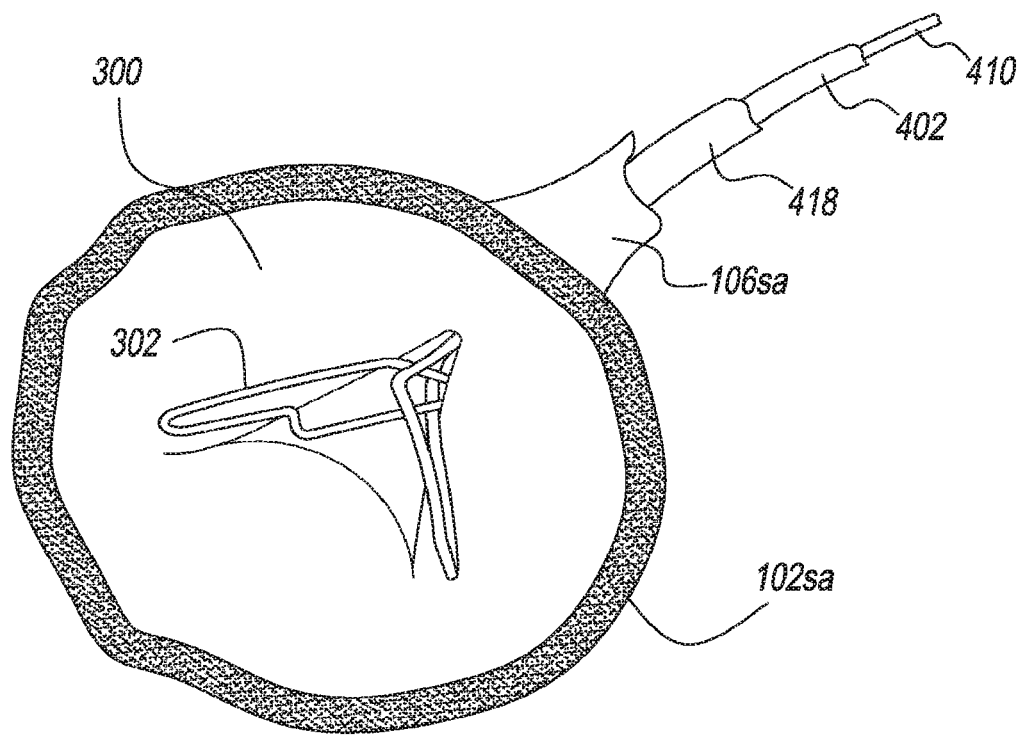

Then, under vision, using the cystoscope 402, the prostatic implant 300 is positioned in the prostatic urethra 106sa along the length of the prostate lobes, as shown in part, in FIG. 8K. The prostatic implant 300 positioning in the prostatic urethra 106sa may include at least one of the following steps, not necessarily in same order:

Rotating the prostatic implant 300, by applying torque forces, relative to the spinal longitudinal axis 312 so as to align the spine member 310 with the anterior interlobar groove of the prostatic urethra 106sa, or/and to align the first elongated edge member 314 with the left posterolateral interlobar groove of the prostatic urethra 106sa, or/and to align the second elongated edge member 316 with the right posterolateral interlobar groove of the prostatic urethra 106sa.

Pulling the prostatic implant 300 in a caudal direction to a position within the prostatic urethra 106sa or/and placing the first and second craniolateral corners 304a and 304b, respectively, against a narrowing imposed by the internal urethral sphincter adjacent to the urinary bladder neck 108sa.

Inserting the spine member 310 in the anterior interlobar groove of the prostatic urethra 106sa, or/and inserting the first elongated edge member 314 in the left posterolateral interlobar groove of the prostatic urethra 106sa, or/and inserting the second elongated edge member 316 in the right posterolateral interlobar groove of the prostatic urethra 106sa.

Visually verifying the alignment using cystoscopy (with the cystoscope 402).

Figure 8L:
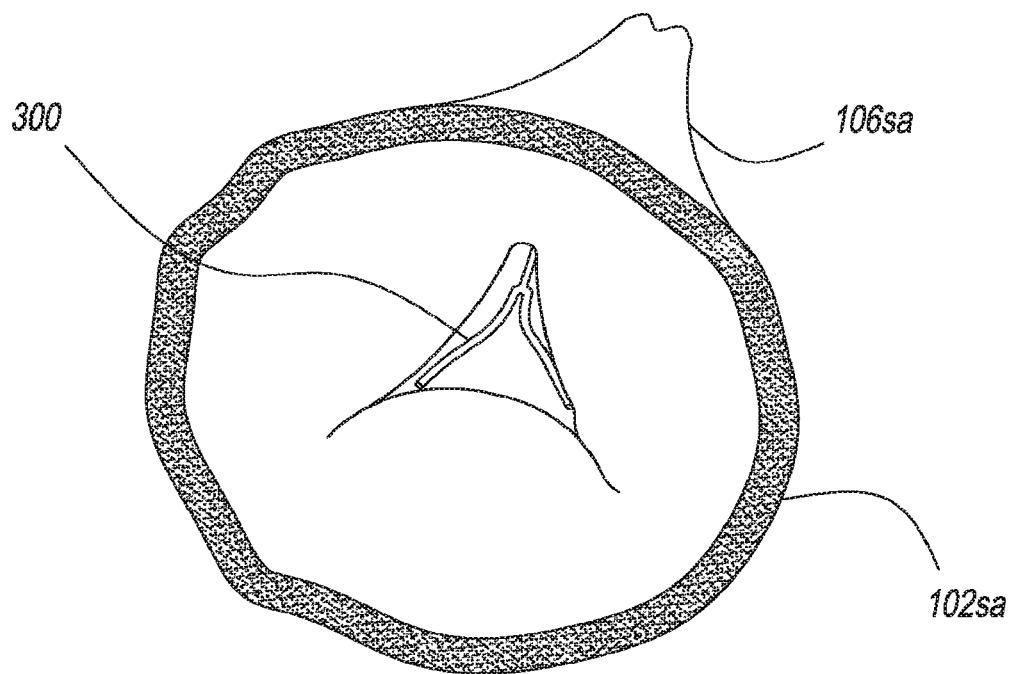

The prostatic implant 300 positioning should result, if the prostatic implant 300 is in its partially collapsed (partially folded/partially unfolded) positioning configuration, in effecting expansion of a distal region of the prostatic urethra 106sa, using the distal retractor 302, into a greater lumen size than an adjacent proximal region of the prosthetic urethra 106sa. The distal retractor 302 may also be partially collapsed into conformity with anatomy of the distal region of the prostatic urethra 106sa. FIG. 8L provides a frontal (caudally directed) view for an exemplary representation of proper positioning of the prostatic implant 300 within the prostatic urethra 106sa. By also expanding (unfolding) the proximal retractor 306, the configuration of the prostatic implant 300 can be changed from the fully collapsed (fully folded) delivery configuration into an expanded (fully unfolded) deployed configuration. Optionally, in exemplary embodiments, such expansion (unfolding) of the prostatic implant 300 is effected in a partial manner, whereby at least most, but not necessarily all, of the prostatic implant 300 structural members change into a fully expanded (unfolded) configuration, for example, possibly due to physical size and dimensional restrictions imposed by the in-vivo environment of the periurethral tissue and the surrounding prostatic lobes. The expansion (unfolding) procedure results in the first and second craniolateral corners 304a and 304b, respectively, to become distanced apart from each other, and, the first and second caudolateral corners 308a and 308b, respectively, to become distanced apart from each other as well. The first and second tissue support members 322 and 324, respectively, of the prostatic implant 300 are also released for supporting respective portions of the lateral prostatic lobes following implant positioning.

The cystoscope 402 is then removed from the prostatic urethra 106sa, and from the entire urethra of the subject, while keeping the over-sheath 418 in place.

Any of the hereinabove illustratively described steps or procedures of the herein disclosed exemplary embodiments of a method (prostatic implant method) for retracting or/and supporting periurethral tissue enclosing a prostatic urethra along a length of prostate lobes, may be repeated in case there is a need to change (e.g., correct) positioning of the prostatic implant 300, or of any portion or member thereof, in relation to chosen anatomical or/and physiological considerations. Repeating any of the previous steps may include, be preceded by, or be followed by, re-collapsing the prostatic implant 300 back into the fully collapsed delivery configuration or/and passing the prostatic implant 300 back into the urinary bladder 102sa. Repeating may be persistent until reaching a chosen result. The chosen result can be verified under vision, for example, using the cystoscope 402.

The chosen result may include anchoring different portions of the prostatic implant 300 in at least two of the anterior interlobar grooves, the left posterolateral interlobar groove, and the right posterolateral interlobar groove, of the prostatic urethra 106sa, within the boundaries of the prostate lobes. The chosen result may also include lifting both prostatic lateral lobes so as to enlarge minimal lumen size of the prostatic urethra 106sa, optionally, to at least 1 mm, or at least 2 mm, along a continuous length of the prostatic urethra, optionally along its entire length, optionally, by shifting each of the prostatic lateral lobes, pivotally, relative to the anterior interlobar groove.

Once it is verified that the prostatic implant 300 is in appropriate positioning within the prostatic urethra 106sa, final deployment and implantation stages can take place, and the prostatic implant 300 should be left therein, with no further interaction with the implant manipulator 410. Accordingly, the fully deployed and implanted prostatic implant 300 is thereby configured and positioned to continuously exert radially directed pushing forces upon the anterior interlobar groove and at least one of the left and right posterolateral interlobar grooves. This may facilitate preventing or minimizing possible axial or/and rotational movement of the prostatic implant 300, or/and to increase distance separating the superior interlobar grooves and to increase distance separating the left and right inferior-lateral interlobar grooves. Such may also facilitate the prostatic implant 300 to exert lateral pressing forces upon each prostatic lateral lobe, thereby, retracting or/and supporting the periurethral tissue.

Figure 8M:
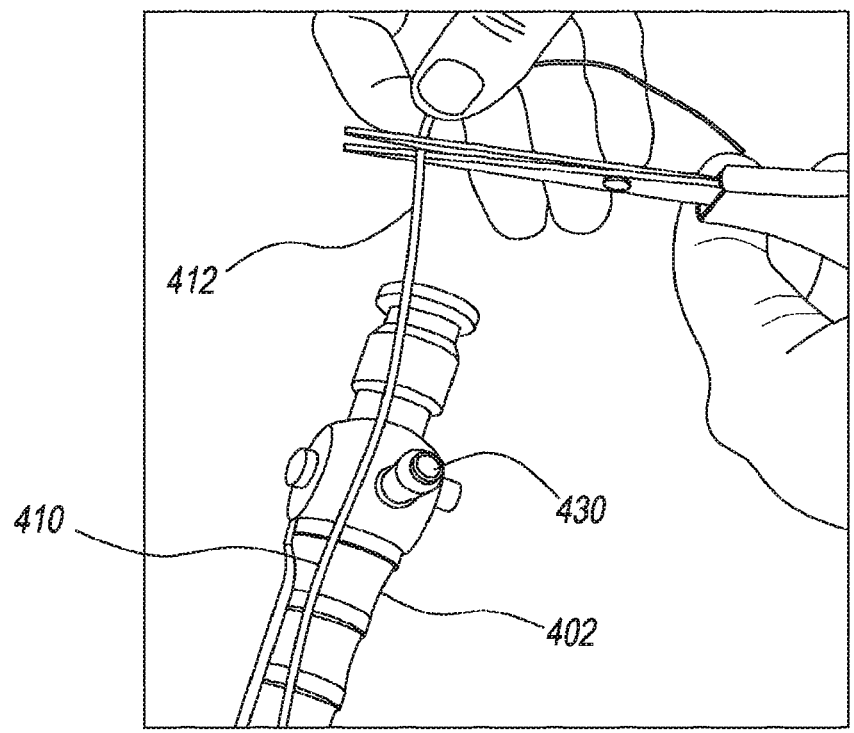
Figure 8N:
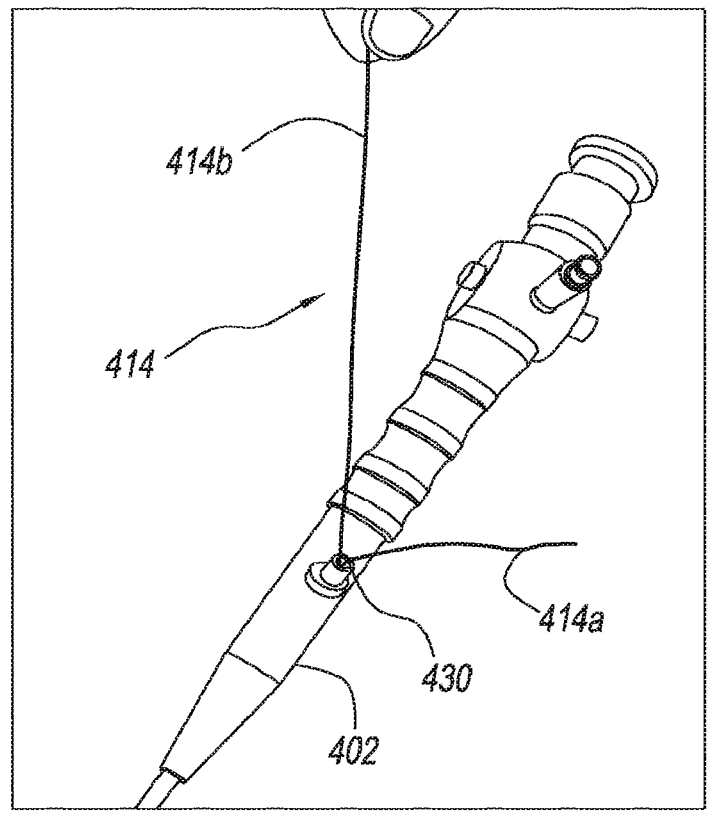

As shown in FIGS. 8M and 8N, the implant manipulator 410 is taken apart into its main parts, namely, the tubular member 412 and the tether 414 (partly shown in FIG. 8M, illustrating scissoring of the implant manipulator 410), and the tether 414 is pulled and withdrawn from holding the prostatic implant 300 and subsequently, from the subject's body (FIG. 8N).

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of' and 'consists of', as used herein, means 'including and limited to'.

The phrase 'consisting essentially of', as used herein, means that the stated entity or item (system, system unit, system sub-unit, device, assembly, sub-assembly, mechanism, structure, component, element, or, peripheral equipment, utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional 'feature or characteristic' being a system unit, system sub-unit, device, assembly, sub-assembly, mechanism, structure, component, or element, or, peripheral equipment, utility, accessory, or material, step or procedure, sub-step or sub-procedure), but only if each such additional 'feature or characteristic' does not materially alter the basic novel and inventive characteristics or special technical features, of the claimed entity or item.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or to dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

The phrase 'operatively connected', as used herein, equivalently refers to the corresponding synonymous phrases 'operatively joined', and 'operatively attached', where the operative connection, operative joint, or operative attachment, is according to a physical, or/and electrical, or/and electronic, or/and mechanical, or/and electro-mechanical, manner or nature, involving various types and kinds of hardware or/and software equipment and components.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. An implant for retracting or/and supporting periurethral tissue enclosing a prostatic urethra comprising:
    a first elongated edge member including a first craniolateral corner;
    a second elongated edge member including a second craniolateral corner said second elongated edge member symmetrically opposed to said first elongated edge member relative to a spinal longitudinal axis;
    a pair of interconnecting members connected at said spinal longitudinal axis; a first of said pair of interconnecting members connected to said first elongated edge member and a second of said pair of interconnecting members to said second elongated edge member;
    a first distal retractor incorporating said first and a second craniolateral corners; and
    a first elastic portion incorporated in said first elongated edge member; and
    a second elastic portion incorporated in said second elongated edge member;
    wherein said first and second elastic portions are non-stressed when said first elongated edge member is pivotally positioned centrally away from said second elongated edge member about said spinal longitudinal axis, so as to form a predetermined maximal spanning angle;
    wherein said at least one of said first and second elastic portions exhibits an increase in stress in response to an increased moment of force pivotally shifting said first elongated edge member towards said second elongated edge member about said spinal longitudinal axis.

2. An implant for retracting or/and supporting periurethral tissue enclosing a prostatic urethra, the implant comprising:
    a spinal longitudinal axis;
    a first elongated edge member and
    a second elongated edge member symmetrically opposed to said first elongated edge member laterally relative to said spinal longitudinal axis;
    at least one pair of interconnecting members connecting said first elongated edge member to said second elongated edge member across said spinal longitudinal axis symmetrically distanced laterally on opposite sides of said spinal longitudinal axis and said first and second elongated edge members equally displaced in a posterior direction with respect to said spinal longitudinal axis such that when said implant is positioned in the prostatic urethra, said first elongated edge member engages a left posterolateral interlobar groove that extends between a left prostatic lateral lobe and a prostatic medial lobe, and said second elongated edge member engages a right posterolateral interlobar groove that extends between a right prostatic lateral lobe and said prostatic medial lobe and said spinal longitudinal axis is aligned to an anterior interlobar groove, and,
    wherein said implant is configured to continuously exert a radially directed pushing force between said first and second elongated edge members, within a range of between about 100 grams and about 1,000 grams, so as to maintain a lumen size of at least 1 mm in said prostatic urethra by and inhibit rotational movement of said implant with respect to said anterior interlobar groove, and, said left and right posterolateral interlobar grooves.

3. A system for retracting or/and supporting periurethral tissue enclosing a prostatic urethra along a length of prostate lobes, the system comprising:
    an implant comprising a plurality of elongated edge members interconnected in a form of a collapsible-expandable frame expandable to support periurethral tissue by exerting pushing forces upon interlobar grooves located along the prostatic urethra, wherein a first one of said elongated edge members includes a first craniolateral corner and a first caudolateral corner, and a second one of said elongated edge members includes a second craniolateral corner opposing said first craniolateral corner and a second caudolateral corner opposing said first caudolateral corner; and
    an implant manipulator detachably connected to said implant first and second elongated edge members, and configured to manipulate and force said first and second caudolateral corners into close proximity with each other and
    wherein said implant manipulator comprises a tubular member and a tether releasably intertwined through both of said implant first and second caudolateral corners, said implant manipulator is configured for pulling said implant via an operator using said tether against a distal end of said tubular member.

4. The implant of claim 1, further comprising:
    at least one tissue support member extending between said first elongated edge member and said spinal longitudinal axis, and at least one other tissue support member extending between said second elongated edge member and said spinal longitudinal axis, wherein each said tissue support member is sized and configured for supporting a portion of a lobe of prostatic lateral lobes when said spinal longitudinal axis engages an anterior interlobar groove that extends between said prostatic lateral lobes, and when said first and second elongated edge members engage corresponding posterolateral interlobar grooves.

5. The implant of claim 1, wherein a length of said implant along said spinal longitudinal axis is less than length of each of said first and second elongated edge members.

6. The implant of claim 2, wherein a length of the implant along said spinal longitudinal axis is less than length of each of said first and second elongated edge members.

7. The implant of claim 2, wherein each of said pair of interconnecting members includes at least one elastic portion adjoining said spinal longitudinal axis, said elastic portion being non-stressed when said first and second elongated edge members are pivotally positioned centrally away from each other about said spinal longitudinal axis, so as to form a predetermined maximal spanning angle between opposing members of said pair of interconnecting members.

8. The implant of claim 7, wherein said predetermined maximal spanning angle is within a range of between 60 degrees and 140 degrees.

9. The implant of claim 7, wherein said at least one elastic portion exhibits an increase in stress when subjected to a moment of force that pivotally shifts said first and second elongated edge members towards each other about said spinal longitudinal axis.

10. The implant of claim 7, wherein said first and second elongated edge members are configured to approach each other so as to form a spanning angle between said pair of interconnecting members being equal to or greater than about 60 degrees, when each said first and second elongated edge member exert a total lateral pressing force upon a corresponding lobe of said prostatic left and right lateral lobes, said total lateral pressing force being a range of between about 100 grams and about 1,000 grams.

11. The implant of claim 2, further comprising
at least one tissue support member extending between said first elongated edge member and said spinal longitudinal axis, and at least one other tissue support member extending between said second elongated edge member and said spinal longitudinal axis, wherein each said tissue support member is sized and configured for supporting a portion of a lobe of prostatic lateral lobes when said spinal longitudinal axis in aligned to an anterior interlobar groove that extends between said prostatic lateral lobes, and when said first and second elongated edge members engage corresponding posterolateral interlobar grooves and wherein said at least one tissue support member is configured as a curvilinear portion of said first elongated edge member protruding towards said spinal longitudinal axis.

12. The implant of claim 2, further comprising:
at least one tissue support member is-configured as a curvilinear portion of said first elongated edge member that protrudes laterally outwardly from an area encompassed by said first elongated edge member and said spinal longitudinal axis.

13. The implant of claim 2, further comprising:
at least one tissue support member configured as a rib extending from one member of said pair of interconnecting members.

14. The implant of claim 13, wherein said rib is curved or bent laterally outwardly from a perimeter of area encompassed by a corresponding member of said first and second elongated edge member and said spinal longitudinal axis.

15. The implant of claim 2, further comprising
at least one tissue support member including a tissue contacting surface sized and shaped according to dimensions of said left and right prostatic lateral lobe portion.

16. The implant of claim 2, configured to anchor said anterior interlobar groove, and, said left and right posterolateral interlobar grooves, by continuously exerting a radially directed pushing force thereupon, so as to increase distance separating superior portions of said left and right interlobar grooves and increase distance separating left and right inferior portions of said left and right interlobar grooves, or/and to maintain a distance of at least 2 mm between said left and right prostatic lateral lobes, by exerting lateral forces thereupon within a range of between about 100 grams and about 1,000 grams.

17. The implant of claim 2, wherein at least one of said first and second elongated edge members comprises a cranial-nose portion shaped and configured for resting against a ledge, imposed by a urinary bladder neck segment adjacent the prostatic urethra, so as to prevent cranial dislodgement of the implant into urinary bladder, when said the implant engages an anterior interlobar groove that extends between said prostatic lateral lobes along said spinal longitudinal axis, and when said first and second elongated edge members engage corresponding posterolateral interlobar grooves.

18. The implant of claim 17, wherein said cranial-nose portion is 'L' shaped.

19. The implant of claim 2, wherein at least one of said first and second elongated edge members comprises a caudal-nose portion shaped and configured for resting against a narrowing, imposed by external urethral sphincter adjacent to verumontanum of the prostatic urethra, so as to prevent caudal migration of the implant through external sphincter and into bulbar urethra, when the implant engages along said spinal longitudinal axis an anterior interlobar groove that extends between said prostatic lateral lobes, and when said first and second elongated edge members engage corresponding posterolateral interlobar grooves.

20. The implant of claim 19, wherein said caudal-nose portion is "L" shaped.

21. The implant of claim 1, wherein said first elongated edge member includes a first caudolateral corner and said second elongated edge member includes a second caudolateral corner and wherein said implant is configured for sequentially changing shape according to deployment configurations including at least one of:
a fully collapsed delivery configuration, whereby said first and second craniolateral corners are in close proximity with each other, and, said first and second caudolateral corners are in close proximity with each other;
a partially collapsed positioning configuration, whereby said first and second craniolateral corners are distanced apart from each other, and, said first and second caudolateral corners are in close proximity with each other; and
an expanded deployed configuration, whereby said first and second craniolateral corners are distanced apart from each other, and, said first and second caudolateral corners are distanced apart from each other.

22. The system of claim 3, wherein said implant manipulator, when connected to said implant, is configured for applying thereto rotational forces, pulling forces.

23. The system of claim 3, further comprising an over sheath sized for covering a length of a cystoscope having a cystoscope lumen dimensioned to restrain said implant in a fully collapsed delivery configuration via at least encircling said implant first and second craniolateral corners.

24. The system of claim 3, wherein said implant manipulator is configured for effecting progressively changing shape of said implant according to different said implant deployment configurations.

25. The system of claim 23, wherein said implant manipulator is configured for manipulating and shifting said implant within said over-sheath between a fully collapsed delivery configuration and a partially collapsed positioning configuration, by pushing said implant relative to said over-sheath until said implant first and second craniolateral corners are released from said implant manipulator over sheath.

26. The system of claim 3, wherein said implant manipulator is configured for manipulating and shifting said implant between a partially collapsed delivery configuration and an expanded deployed configuration by detaching from said implant after release of said tether from said implant first and second caudolateral corners.

27. The implant of claim 21, wherein in said partially collapsed positioning configuration said implant has a maximum diameter on a distal portion thereof that is greater than a smallest cross-sectional dimension in a urinary bladder neck joining the prostatic urethra, and wherein said partially collapsed positioning configuration said implant has a minimum diameter on a proximal portion thereof that is smaller than said smallest cross-sectional dimension in said urinary bladder neck.

28. The implant of claim 1, further comprising:
an elongated spine member along said spinal longitudinal axis; and
where said first elongated edge member and said second elongated edge member are interconnected to said elongated spine member via said pair of interconnecting members.

29. The implant of claim 28, wherein a length of said elongated spine member is less than length of each of said first and second elongated edge members.

30. The implant of claim 1, wherein said first and second craniolateral corners are shaped and configured for resting against a ledge imposed by urinary bladder neck so as to prevent cranial dislodgement of said implant into urinary bladder, when said spinal longitudinal axis engages an anterior interlobar groove that extends between prostatic lateral lobes, and when said first and second elongated edge members engage corresponding posterolateral interlobar grooves.

31. The implant of claim 21, wherein at least one of said first and second caudolateral corners are shaped and configured for resting against a narrowing imposed by external urethral sphincter adjacent verumontanum of the prostatic urethra, so as to prevent caudal shift of said implant, when said spinal longitudinal axis engages an anterior interlobar groove that extends between prostatic lateral lobes, and when said first and second elongated edge members engage corresponding posterolateral interlobar grooves.

32. The implant of claim 31, wherein each of said first and second caudolateral corners has a shape or form of a proximally directed apex, said apex being formed by intersection of converging curved slopes of respective ones of said implant first and second caudolateral corners.

33. The implant of claim 1, wherein said first elongated edge member includes
a first caudolateral corner and said second elongated edge member includes a second caudolateral corner and wherein said implant is configured for progressively changing shape according to deployment configurations including:
a fully collapsed delivery configuration, whereby said first and second craniolateral corners are in close proximity with each other, and, said first and second caudolateral corners are in close proximity with each other;
a partially collapsed positioning configuration, whereby said first and second craniolateral corners are distanced apart from each other, and, said first and second caudolateral corners are in close proximity with each other; and
an expanded deployed configuration, whereby said first and second craniolateral corners are distanced apart from each other, and, said first and second caudolateral corners are distanced apart from each other.

34. The system of claim 3, wherein said implant manipulator, when connected to said implant, is configured for applying thereto pulling forces.

35. The system of claim 3, wherein said implant manipulator, when connected to said implant, is configured for applying thereto pushing forces.

36. The implant of claim 29, wherein said first elongated edge member and second elongated edge member are symmetrically distanced from each other laterally across said spinal longitudinal axis and displaced equally in a posterior direction with respect to said spinal longitudinal axis for positioning said first elongated edge member in a left posterolateral interlobar groove that extends between a left prostatic lateral lobe and a prostatic medial lobe, and said second elongated edge member in a right posterolateral interlobar groove that extends between a right prostatic lateral lobe and said prostatic medial lobe; said implant sized to maintaining a lumen size of at least 1 mm in said prostatic urethra.

* * * * *